United States Patent
Siess et al.

(10) Patent No.: US 10,780,208 B2
(45) Date of Patent: Sep. 22, 2020

(54) BLOOD PUMP

(71) Applicant: Abiomed Europe GMBH, Aachen (DE)

(72) Inventors: Thorsten Siess, Aachen (DE); Walid Aboulhosn, Aachen (DE); Wolfgang Kerkhoffs, Aachen (DE); Ellen Keysselitz, Aachen (DE); Peter Skrodsky, Aachen (DE)

(73) Assignee: ABIOMED EUROPE GMBH, Aachen (DE)

( * ) Notice: Subject to any disclaimer, the term of this patent is extended or adjusted under 35 U.S.C. 154(b) by 0 days.

(21) Appl. No.: 15/750,001

(22) PCT Filed: Aug. 3, 2016

(86) PCT No.: PCT/EP2016/068576
§ 371 (c)(1),
(2) Date: Feb. 2, 2018

(87) PCT Pub. No.: WO2017/021465
PCT Pub. Date: Feb. 9, 2017

(65) Prior Publication Data
US 2018/0228953 A1    Aug. 16, 2018

(30) Foreign Application Priority Data

Aug. 4, 2015    (EP) .................................. 15179624

(51) Int. Cl.
*A61M 1/10* (2006.01)
*A61M 1/12* (2006.01)

(52) U.S. Cl.
CPC ........ *A61M 1/1036* (2014.02); *A61M 1/1017* (2014.02); *A61M 1/125* (2014.02)

(58) Field of Classification Search
CPC .. A61M 1/1036; A61M 1/1017; A61M 1/125; A61M 1/10; A61M 1/1001; A61M 1/1003
See application file for complete search history.

(56) References Cited

U.S. PATENT DOCUMENTS

2011/0008149 A1    1/2011    Jarvik
2012/0089225 A1*    4/2012    Akkerman .......... A61M 1/1017
                                                            623/3.13

FOREIGN PATENT DOCUMENTS

EP            2525099 A1    11/2012
JP        2013099536 A      5/2013
(Continued)

OTHER PUBLICATIONS

International Search Report dated Sep. 21, 2016, for International Application No. PCT/EP2016/068576 (4 pages).
(Continued)

*Primary Examiner* — Paula J Stice
(74) *Attorney, Agent, or Firm* — Botos Churchill IP Law LLP

(57) ABSTRACT

A blood pump comprises a pump casing having a blood flow inlet and a blood flow outlet, and an impeller arranged in said pump casing and rotatably supported in the pump casing by a bearing so as to be rotatable about an axis of rotation. The impeller has blades for conveying blood from the blood flow inlet to the blood flow outlet. The bearing comprises at least one stationary bearing portion coupled to the pump casing and having a stationary bearing surface that faces radially outwards. The bearing further comprises a rotating bearing surface interacting with the stationary bearing surface to form the bearing, wherein the rotating bearing surface faces radially inwards and is formed on an exposed radially inner edge of the blades. The blades are designed to draw blood deposit on the stationary bearing surface in a radially outward direction.

27 Claims, 28 Drawing Sheets

(56) References Cited

FOREIGN PATENT DOCUMENTS

| WO | 98/11347 | 3/1998 |
| WO | 01/70300 A1 | 9/2001 |
| WO | 2006/137496 A1 | 12/2006 |

OTHER PUBLICATIONS

Japanese Office Action issued in corresponding JP application No. 2018-506093 dated Mar. 24, 2020.

* cited by examiner

BLOOD PUMP

CROSS-REFERENCE TO RELATED APPLICATIONS

This application is a United States National Stage filing under 35 U.S.C. § 371 of International Application No. PCT/EP2016/068576, filed Aug. 3, 2016, which claims the benefit of European Patent Application No. 15179624.0, filed Aug. 4, 2015, the contents of all of which are incorporated by reference herein in their entirety. International Application No. PCT/EP2016/068576 was published under PCT Article 21(2) in English.

BACKGROUND

This invention relates to a blood pump, in particular an intravascular blood pump, to support a blood flow in a patient's blood vessel.

Blood pumps of different types are known, such as axial blood pumps, centrifugal blood pumps or mixed-type blood pumps, where the blood flow is caused by both axial and radial forces. Intravascular blood pumps are inserted into a patient's vessel such as the aorta by means of a catheter. A blood pump typically comprises a pump casing having a blood flow inlet and a blood flow outlet. In order to cause a blood flow from the blood flow inlet to the blood flow outlet, an impeller or rotor is rotatably supported within the pump casing about an axis of rotation, with the impeller being provided with one or more blades for conveying blood.

The impeller is usually supported within the pump casing by means of at least one bearing. A variety of bearings are known, such as contact-type bearings and non-contact bearings. Generally, contact-type bearings may include all types of bearings in which the bearing surfaces may have at least partial contact during operation of the pump at any time (i.e. always or intermittently), e.g. slide bearings, pivot bearings, hydrodynamic bearings, hydrostatic bearings, ball bearings, etc., or any combination thereof. In particular, contact-type bearings may be "blood immersed bearings", where the bearing surfaces have blood contact. Contact-type bearings may heat up during use and are subject to mechanical wear caused by the contact of the rotating and static bearing surfaces during operation of the pump. It is desirable to supply a cooling fluid to the bearing, such as the blood itself. Arrangements for flushing clearances or bearing surfaces within a blood pump are disclosed for instance in US 2011/0238172 A1. Wash-out channels extend through the impeller and are in fluid communication with the main blood flow passage and the bearing surfaces.

SUMMARY OF THE INVENTION

It is an object of the present invention to provide a blood pump that allows for effective cooling and flushing of a bearing that rotatably supports the impeller of the blood pump.

This object is achieved according to the present invention by a blood pump having the features of independent claim 1. Preferred embodiments and further developments of the invention are specified in the claims dependent thereon.

According to the invention the impeller is rotatably supported in the pump casing by at least one bearing. The bearing comprises at least one stationary bearing portion coupled to the pump casing and having a stationary bearing surface that faces radially outwards, the bearing further comprising a rotating bearing surface interacting with the stationary bearing surface to form the bearing, wherein the rotating bearing surface faces radially inwards and is formed on an exposed radially inner edge of at least one of the blades or on a bearing structure coupled to the exposed radially inner edge of the blades. Using exposed radially inner edges of the blades for the bearing allows for an open bearing design that can improve flushing of the bearing surfaces. Thus, heating of the bearing can be reduced. Likewise, blood clogging and clotting in the bearing area can be reduced. In particular, having the inner edge of the rotating blade acting as the mating part of the bearing has the intrinsic advantage of centrifuging the blood boundary layer radially away from the bearing surfaces. That is to say, centrifugal forces are created that help to draw blood deposit, which has a greater density than the flowing blood, away from the stationary bearing surface in a radially outward direction. Thus, the design of the bearing helps to wash out the mating surfaces of the bearing.

Preferably, the stationary bearing portion comprises at least one pin or cone extending along the axis of rotation. The stationary bearing portion may be substantially cylindrical or tapered in shape and may vary in length along the axis of rotation. For example, the stationary bearing portion may extend axially along less than half of the length of the impeller or it may extend substantially along the entire length of the impeller. In particular if the stationary bearing portion is relatively short, the bearing may comprise two stationary bearing portions axially extending towards or into the impeller from opposing axial ends of the impeller.

Regardless of the specific design and shape of the stationary bearing portion, the stationary bearing portion may be denoted as a "pin", and the bearing may be denoted as a "pin bearing". These terms will not be limited to a specific pin design but will refer to all types of stationary bearing portions and blade arrangements within the scope of the present invention, i.e. in particular a stationary bearing portion having a radially outwards facing bearing surface interacting with an exposed radially inner edge of an impeller blade.

The rotating bearing surface may extend along substantially the entire length of the exposed radially inner edge of the at least one blade. This results in a large bearing surface, which is advantageous e.g. for heat dissipation. The fact that the bearing is formed on the blades, which may offer high heat dissipation themselves, also improves heat dissipation. Alternatively, it may extend only along a portion of the length of the exposed radially inner edge of the blade. In particular, in order to reduce the size of the contact area between the stationary and rotating bearing surfaces, the rotating bearing surface may be formed as one or more separate segments along the exposed radially inner edges of the blades. This may be achieved e.g. by a specific uneven profile of the inner blade edges, where the bearing surface may be formed by raised portions of the profile, or by coatings, inserts or the like. Specific materials could be used for coatings and inserts as described in more detail below.

In one embodiment, the stationary bearing portion may have a central axial passage extending therethrough. For example, the stationary bearing portion or pin may have an axial channel. This allows blood to flow to an axial end surface of the pin in order to wash out a clearance between the pin and the impeller. Furthermore, if the impeller has a central axial passage, too, blood can flow from the pin passage into the impeller passage.

The stationary bearing portion may be coupled to the pump casing by means of a supporting structure that comprises at least one aperture to allow blood to pass therethrough in an axial direction. For example, the stationary bearing portion may be supported by struts that are connected to the pump casing. This can be particularly useful if the stationary bearing portion is placed in a region of the blood flow inlet since it allows the pin to be arranged in the blood flow inlet, while blood can enter the pump casing through the apertures defined by the struts. This may also apply to the blood flow outlet in case blood is desired to exit the pump casing in an axial direction. Alternatively or in addition, the supporting structure may be sized and shaped to direct a blood flow in a radial direction. The supporting structure may have for instance a tapered shape such as a straight or curved cone that forms a socket for the pin, the supporting structure widening in a downstream direction and arranged near the blood flow outlet.

Generally, the above described pin bearing concept applies to different designs of the impeller, and in particular the at least one blade, as long as the rotating bearing surface is formed on an exposed radially inner edge of the blades or possibly on a bearing structure coupled to an exposed radially inner edge of the blades. In particular, the at least one blade may be attached to an outer surface of the impeller hub, an inner surface of the impeller hub, or both. If the blades are located on an outer surface of the hub, the exposed radially inner edge may be located in a region of the blades that axially extends beyond the hub. If the blades are located on an inner surface of the hub, they may be regarded as inner blades and may be located in a passage of the impeller as described in detail below. It will be appreciated that a combination of "inner" and "outer" blades can be included in a single impeller.

According to one embodiment, the impeller comprises at least one outer blade disposed on an outer surface of the hub of the impeller and sized and shaped for conveying blood from the blood flow inlet to the blood flow outlet. Furthermore, the impeller of the blood pump has a blood flow passage extending through the impeller hub, with at least one inner blade being disposed in the passage that is sized and shaped for conveying blood through the passage. The rotating bearing surface is provided on an exposed radially inner edge of at least one of the inner blades or at least one of the outer blades or both, the inner and outer blades.

Providing inner blades in the passage of the impeller in addition to the outer blades enables the blood flow from the blood flow inlet towards the blood flow outlet to be supported by the inner blades pumping blood through the blood flow passage of the impeller, in particular if the blood flow through the passage of the impeller is directed in the same direction as the main blood flow from the blood flow inlet to the blood flow outlet ("forward flow direction"). Regardless of the direction of flow in the blood flow passage of the impeller, the overall circulation of blood within the pump casing can be improved by the inner blades, thereby improving the flushing and cooling of clearances, bearing surfaces and other surfaces within the pump casing. The inner blades do not require additional space or an additional driving mechanism because they are disposed in the blood flow passage of the impeller and rotate with the impeller.

Preferably, the inner blades are sized and shaped for conveying blood through the passage to the bearing. In particular, this means that blood may be conveyed by the inner blades to the bearing, into the bearing or along the bearing. The inner blades create an active wash-out flow to the bearing, preferably in the forward flow direction, to flush and cool the bearing, which is particularly advantageous when the bearing is a contact-type bearing. Heat dissipation is maximized. Thus, blood clotting and clogging in the bearing can thereby be effectively reduced or avoided. In a certain pump design a wash-out flow in a "backward flow direction" (i.e. opposite the "forward flow direction") could be advantageous. For example, large-diameter blood pumps could benefit from having a pressure gradient in addition to an inner blade impeller to drive a very high blood backflow without affecting the overall pump flow.

The blood flow passage of the impeller may extend at least partially, preferably completely, axially along at least a portion of the impeller, in particular the impeller hub. When at least a portion of the passage, in particular a portion of the passage in which the inner blades are disposed, is aligned with the axis of rotation, this can improve the pumping of blood by means of the inner blades because the inner blades then rotate about the axis of rotation. Furthermore, the inner blades may physically remove any blood deposit in the bearing area as well as through the action of highly turbulent blood flow in the proximity of the pin bearing surface. In other words, the exposed radially inner edges of the inner blades may act like a wiper blade on the stationary bearing surface of the stationary bearing portion.

The passage of the impeller may have a portion or portions that do not extend along the axis of rotation but are angled with respect to the axis of rotation. In particular, one or more end portions of the passage in the impeller may be angled with respect to the axis of rotation. However, it is preferred that the blood flow passage extends completely through the impeller along the axis of rotation from a first axial end or opening to a second axial end or opening. The inner blades may then pump blood along an axial direction through the blood flow passage of the impeller. If the axial passage extends completely through the impeller along the axis of rotation, the impeller can be regarded as being hollow or having a hollow hub, e.g. as a hollow cylinder or hollow cone, with the outer blades being disposed on the outer surface of the hollow hub and the inner blades being disposed on the inner surface of the hollow hub. It will be appreciated that any other suitable hollow shapes that may not necessarily be strictly cylindrical can be chosen for the impeller, such as substantially cylindrical or tapered or other tubular shapes.

In one embodiment, the bearing may be disposed in the blood flow passage. Positioning the bearing in the passage of the impeller may improve washing out and cooling of the bearing, since the bearing is directly arranged in the blood flow that is pumped through the impeller's passage. The stationary bearing portion may comprise at least one pin extending along the axis of rotation, wherein at least a portion of the pin engages the exposed radially inner edge of the blades, in particular of the inner blades, or engages a bearing structure attached to the exposed radially inner edge of the blades to form the at least one bearing. It will be appreciated that the pin may be substantially cylindrical or may be tapered to form a conical shape. The latter would also allow for compensation of axial forces so that the bearing can act as an axial and radial bearing. The pin may extend only towards or into an end portion of the passage or may extend a larger distance into the passage, for example along at least half, preferably at least three quarters, of the length of the passage of the impeller. In a preferred embodiment, the pin may extend completely through the passage of the impeller, i.e. at least along the entire length of the passage in the impeller. The length of the pin may be greater than the length of the impeller's blood flow passage. Regardless of the length of the pin, a maximum diameter of the pin may be smaller than a minimum diameter of the passage of the impeller. This allows blood to flow through the passage past the pin.

In particular the inner blades may have at least one exposed radially inner edge that defines the rotating bearing surface. That is to say, at least a portion of the radially inner edge of the inner blades may engage at least a portion of the stationary bearing surface, e.g. a circumferential surface of the pin, to form the at least one bearing. Using the inner blades as a bearing structure simplifies the construction of the blood pump because no additional bearing structure is necessary. This is particularly advantageous when the pin extends completely through the passage of the impeller. The edges of the inner blades may contact a circumferential surface of the pin along their entire length or at least along their substantially entire length. In addition, since the inner blades form the dynamic part of the bearing, heat dissipation is maximized especially when the inner blades are made of material that has a high heat transfer rate. Since this bearing extends through the blood flow passage of the impeller, the bearing is effectively cooled and flushed. The inner blades have multiple functions. They act as a pumping means for pumping blood through the passage of the impeller to actively wash out the bearing, while acting as the bearing itself at the same time. Moreover, they act as a heat dissipation surface that is set in a turbulent flow area to maximize heat dissipation. The radially inner edges of the blades may be tapered in the circumferential direction to improve the functionality of a hydrodynamic bearing compared to edges that are parallel to the surface of the pin.

In one embodiment, wherein at least one outer blade and at least one inner blade are provided, the at least one blade of the impeller may be arranged on the impeller hub such that the blade is divided by the hub into an inner portion forming the inner blade and an outer portion forming the outer blade. In other words, the inner blades may be aligned with the outer blades, or the inner blades may form a "continuation" of the outer blades through the hub of the impeller, in particular when the impeller has a hollow hub. In particular, the inner blades and outer blades may have a corresponding size and shape. Regardless of the specific size and shape of the blades, the hollow hub may be continuous or may be interrupted by openings to allow blood to flow from the inner blades to the outer blades or vice versa, which may be advantageous for hydraulic balance. Generally, it is important that the blood flow caused by the inner blades and the blood flow caused by the outer blades are hydraulically balanced. As a result, both blade sets will cause a blood flow in a forward direction, in particular within an operating range of a pressure of up to 200 mmHg.

For example, the inner and outer blades may extend the same distance from the hub of the impeller radially inwards and radially outwards, respectively. This design is simple as it basically defines one set of blades that is separated into inner and outer blades by the hub of the hollow impeller. However, in another embodiment, the inner and outer blades may not be aligned or may not correspond in size and shape. The inner blades may be for instance smaller than the outer blades. The inner and outer blades may differ in entrance angle, exit angle and/or pitch angle depending on the hydraulic requirement. Apart from that, the number of outer blades and the number of inner blades may be the same or may be different, regardless of whether the outer blades and the inner blades are aligned or correspond in size and shape. For example, there may be more inner blades than outer blades, such as three inner blades and two outer blades. It will be appreciated that there may only be a single inner blade or a single outer blade, or there may be two or more inner or outer blades. Generally, if more than one blade is provided, not all of them, such as only one of them, may form part of the bearing, while the other blades may be spaced from the stationary bearing surface. The inner blades or outer blades or both may spiral about the axis of rotation, i.e. they may be of helical shape or vary in pitch. Alternatively, the blades may extend straight in an axial direction.

The inner blades may fully correspond to the outer blades. In fact, it can be achieved that both inner and outer blades form a single blade, which is held in position by an outer hub, so that the blades extend centrally toward the hub and can form together with the central pin a radial bearing. The outer hub may accommodate a set of magnets that form the rotor of the electric motor that is driven by stator coils situated on the outer surface of the pump casing.

In one embodiment, the pump casing may have a secondary blood flow inlet axially spaced from the blood flow inlet and the blood flow outlet in a main direction of flow. For instance, the blood flow inlet may be arranged at an upstream end of the pump casing, and the secondary blood flow inlet may be arranged at an opposing downstream end of the pump casing. However, the secondary blood flow inlet may also be arranged circumferentially in the pump casing. The secondary blood flow inlet may be used for creating a wash-out flow along the impeller. For this purpose, the impeller may comprise at least two blades, at least one of which is associated with the blood flow inlet in order to convey blood from the blood flow inlet to the blood flow outlet in the main direction of flow, and at least another one of which is associated with the secondary blood flow inlet to convey blood from the secondary blood flow inlet to the blood flow outlet in a direction opposite the main direction of flow.

The at least two blades may be arranged at axially opposing portions of the impeller adjacent an intermediate portion of the impeller, and the at least one blade associated with the secondary blood flow inlet is sized and shaped to convey blood along the intermediate portion of the impeller. That is to say, the impeller may be regarded as a "double impeller", with blood being pumped in two opposing directions towards the center of the impeller by opposing blades that are arranged at opposing end portions of the impeller. While the blades that are associated with the blood flow inlet create a main blood flow, the blades associated with the secondary blood flow inlet cause an active wash-out flow along the impeller hub. In this embodiment, the impeller may comprise two of the aforementioned pin bearings at its opposed axial ends, with exposed radially inner edges of the respective blades being supported by a respective pin. The "secondary" blades are used to pull blood from outside the pump and force it through the radial gap between the magnetic drive and the pump casing in order to wash and cool the electric motor formed by the magnetic drive and the stationary stator coils positioned on the outside surface of the pump casing. It will be appreciated that the secondary pump may be designed as an axial, mixed flow or substantially radial pump.

In one embodiment, instead of or in addition to using the exposed radially inner edge of the blades as the rotating bearing surface itself, a bearing structure coupled to the exposed radially inner edge of the blades can be used for the bearing. The rotating bearing surface may be defined by at least one ring engaging at least a portion of the pin. The at least one ring may be provided separately from the inner blades or may be coupled to at least one or all of the inner blades, either in addition to the rotating bearing surface formed by the exposed radially inner edges of the inner blades or alternatively thereto. In other words, the bearing surface of the bearing structure may be formed only by the at least one ring or it may be formed by the at least one ring along with the radially inner edges of the blades.

Alternatively or additionally to the ring, the bearing structure may comprise at least one wing that engages at least a portion of the pin and that may be coupled to at least one or all of the inner blades. The at least one wing may have a circular arc shape that corresponds in size and shape to an outer circumferential surface of the pin to form a bearing that provides in particular radial centering of the impeller. It will be appreciated that the aforementioned rings may be formed of such wings. For example, at least two, such as two, three or four, circumferentially adjacent wings may be connected to form a ring. The wings or rings may be arranged at one or more positions along the length of the impeller's passage. These wings may have a certain geometrical shape to maximize the amount of blood or only blood plasma to enter the bearing area. In addition, the centrifugal force in the vicinity of the pin bearing could be used to move red blood cells and other cellular blood components from the bearing area radially and away from the bearing area.

In another embodiment, the rotating bearing surface may be sized and shaped to engage an axial end of the stationary bearing portion to form the at least one bearing and may be coupled to at least one or all of the blades. The rotating bearing surface may be a continuous surface or may comprise separate segments that may be arranged regularly, e.g. symmetrically with respect to the axis of rotation. The rotating bearing surface may form e.g. a cup, a dome, a hemisphere, a cone or any other suitable rotationally symmetrical surface that corresponds in size and shape to an axial end surface of the pin. This type of bearing provides radial centering of the impeller as well as axial support.

The blood pump preferably is driven by a radial drive, with an electrical arrangement being coupled to the pump casing and circumferentially arranged about the impeller and possibly the pump casing to create a rotating magnetic field. Permanent magnets in the impeller are magnetically coupled to the rotating magnetic field of the stator coil so as to cause rotation of the impeller about the axis of rotation. The magnets may be incorporated in the impeller, in particular in the blades, preferably in the outer blades. A radial drive allows a compact design of the blood pump and can be designed independently of the bearing, in particular the aforementioned pin extending into the passage of the impeller. It will be appreciated, however, that any other suitable drive mechanism can be employed in the blood pump. In particular, drive mechanisms suitable in intravascular catheter pumps are preferred, which are designed for miniaturization and high energy density.

The aforementioned bearing may be supported by an additional bearing. The additional bearing may be particularly designed to bear axial loads in one or both axial directions along the axis of rotation in order to relieve the pin bearing. In one embodiment, the stationary bearing portion and the impeller may each comprise at least one magnet. The magnet in the stationary bearing portion and the magnet in the impeller may be radially aligned and arranged in the stationary bearing portion and the impeller, respectively, such that an axial repulsive magnetic force is caused between the stationary bearing portion and the impeller. Consequently, respective axial end surfaces of the impeller and the stationary bearing portion do not contact each other due to the repulsive magnetic force, such that wear and heating are avoided at the axial end surfaces while the repulsive magnetic force helps in axially aligning the impeller in the pump casing. This can be particularly useful if repulsive magnetic forces act on the impeller from both opposing axial ends in opposite directions.

In one embodiment, at least one of the stationary bearing surface and the rotating bearing surface may comprise a material having a greater hardness than a material of the rest of the stationary bearing portion and the impeller, respectively, to reduce wear of the bearing surfaces. For example, a coating or inserts of a specific material may be used to reduce wear. A suitable material may be ceramics. In order to increase heat dissipation, the blades may be made for instance of metal, while the blades, in particular the rotating bearing surface on the exposed radially inner edges of the blades, may be coated with ceramics, completely or partially, or may have ceramic inserts. Inserts, such as ceramic inserts, could be insert molded or bonded to the inner blade surface contacting the pin surface in order to increase bearing life. Since high heat dissipation is intrinsic to the blades, a high heat generation could be well accommodated without adversely affecting blood deposit in the bearing area or bearing wear. With regard to heat dissipation, silicon carbide may be preferred for the inserts or coating. Also, the mating material may be steel, which may be coated with e.g. a diamond coating. In addition, it is preferred to keep the relative velocity at which the mating parts slide against each other to a minimum, preferably below 1.5 m/s, which corresponds to a shaft diameter of approximately 1 mm for a pump with an outer diameter of 6 mm and a design speed of 30,000 rpm.

In another embodiment, the impeller may include at least one secondary blade disposed at an axial end surface of the impeller. Secondary blades may improve wash-out of bearing surfaces or gaps between the impeller and the pump casing or may provide a hydrodynamic axial bearing when interacting with a respective, preferably smooth, inner surface of the pump casing.

BRIEF DESCRIPTION OF THE DRAWINGS

The foregoing summary, as well as the following detailed description of preferred embodiments, will be better understood when read in conjunction with the appended drawings. For the purpose of illustrating the present disclosure, reference is made to the drawings. The scope of the disclosure is not limited, however, to the specific embodiments disclosed in the drawings. In the drawings.

DETAILED DESCRIPTION

Figure 1:
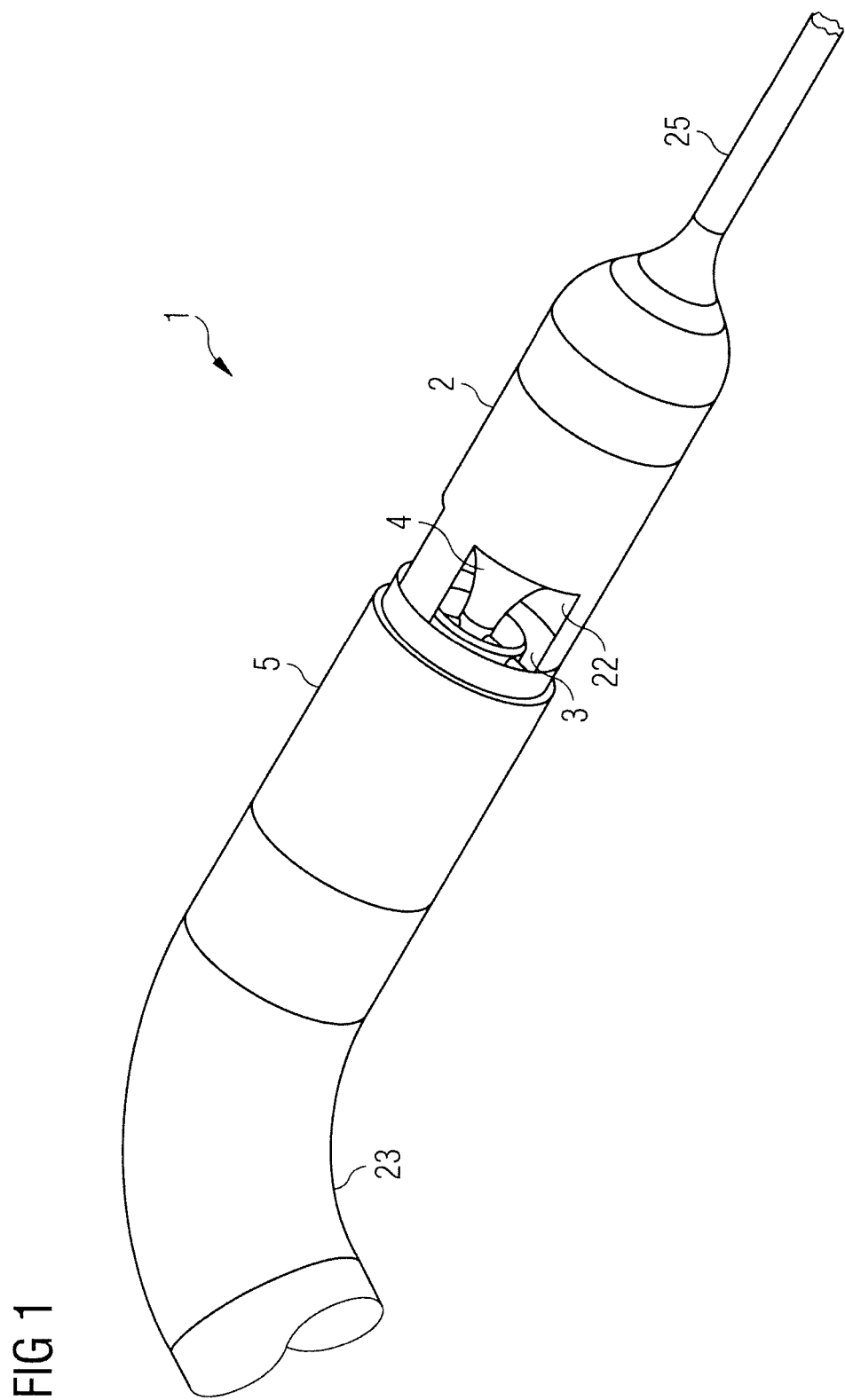
FIG. 1 shows a perspective view of one embodiment of a blood pump.
Figure 2:
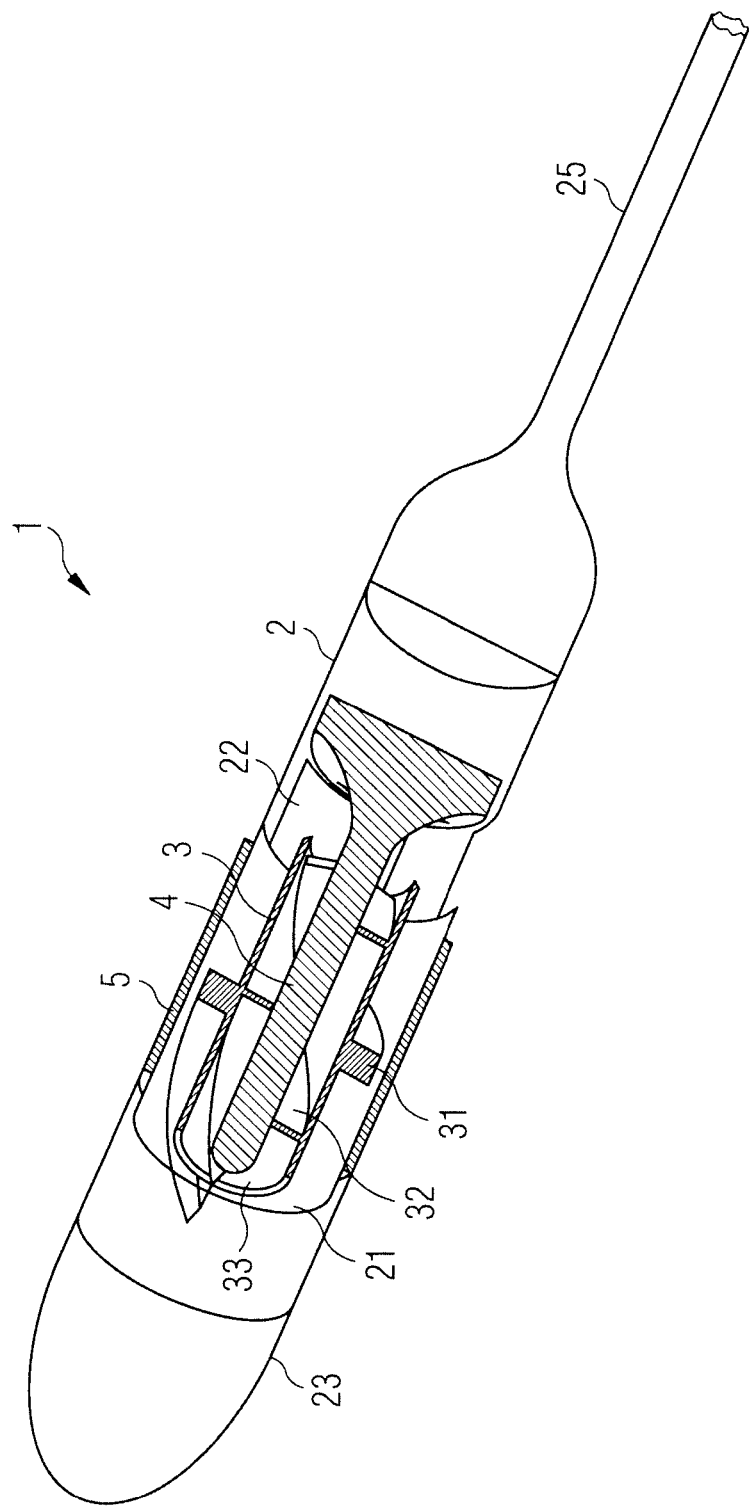
FIG. 2 shows a cross-sectional view of the blood pump of FIG. 1.
Figure 3:
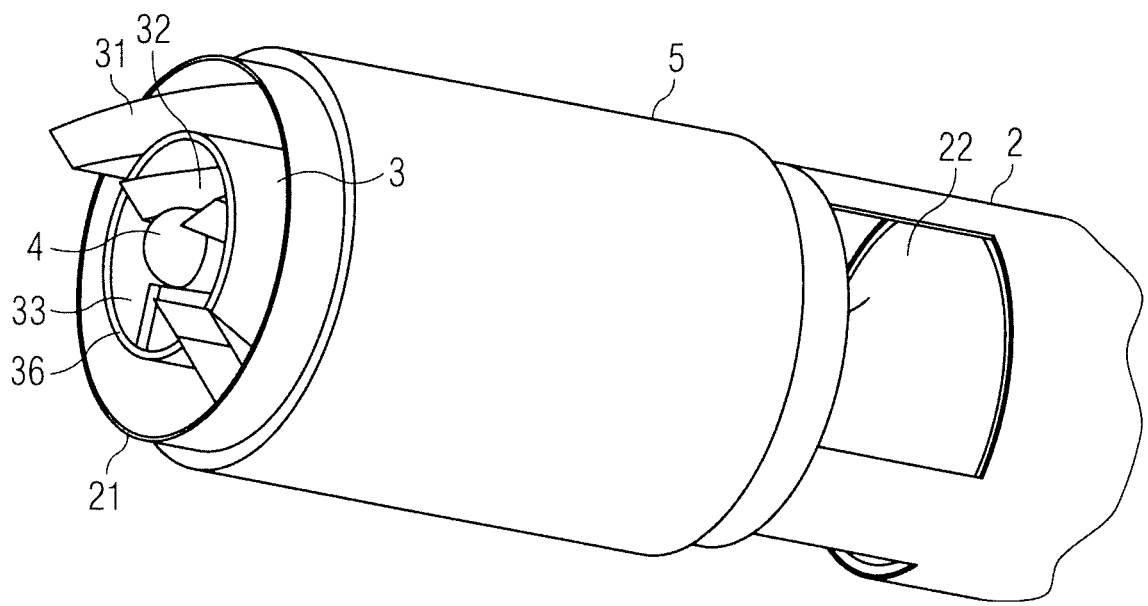
FIG. 3 shows a perspective view of a part of the blood pump of FIG. 1.
Figure 4:
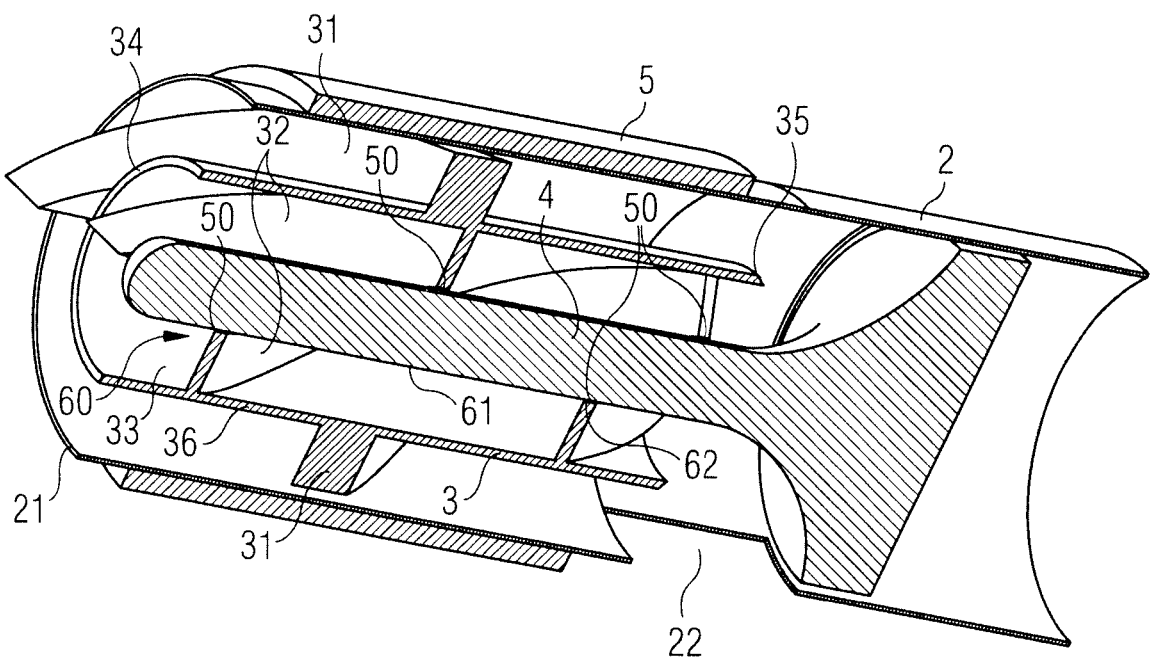
FIG. 4 shows a cross-sectional view of the part shown in FIG. 3.
Figure 5:
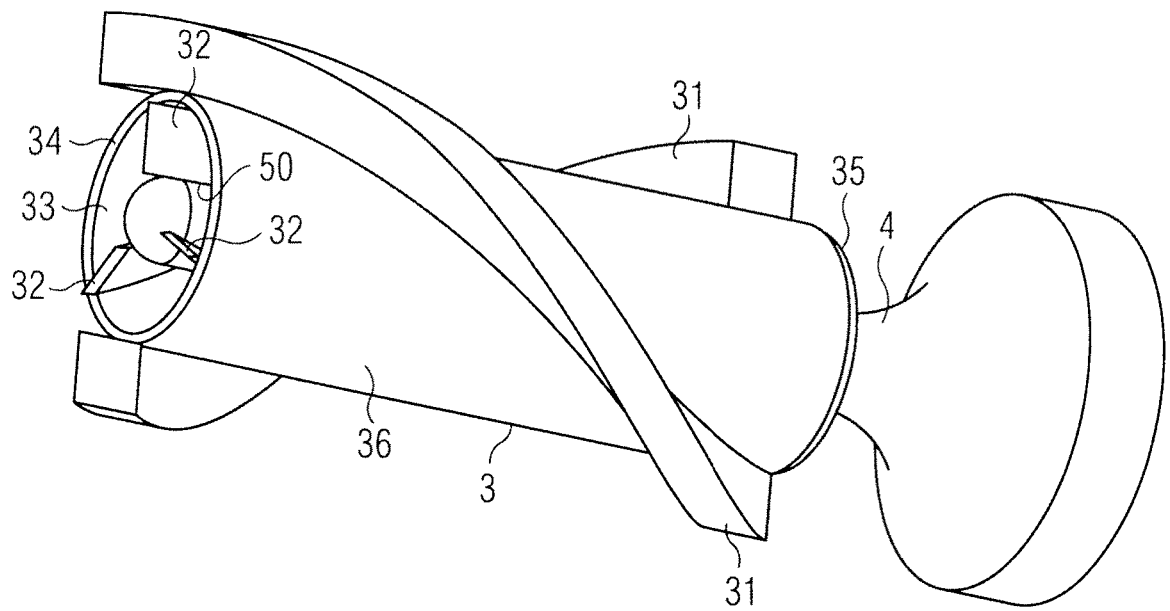
FIG. 5 shows a perspective view of the impeller of the blood pump of FIG. 1.
Figure 6:
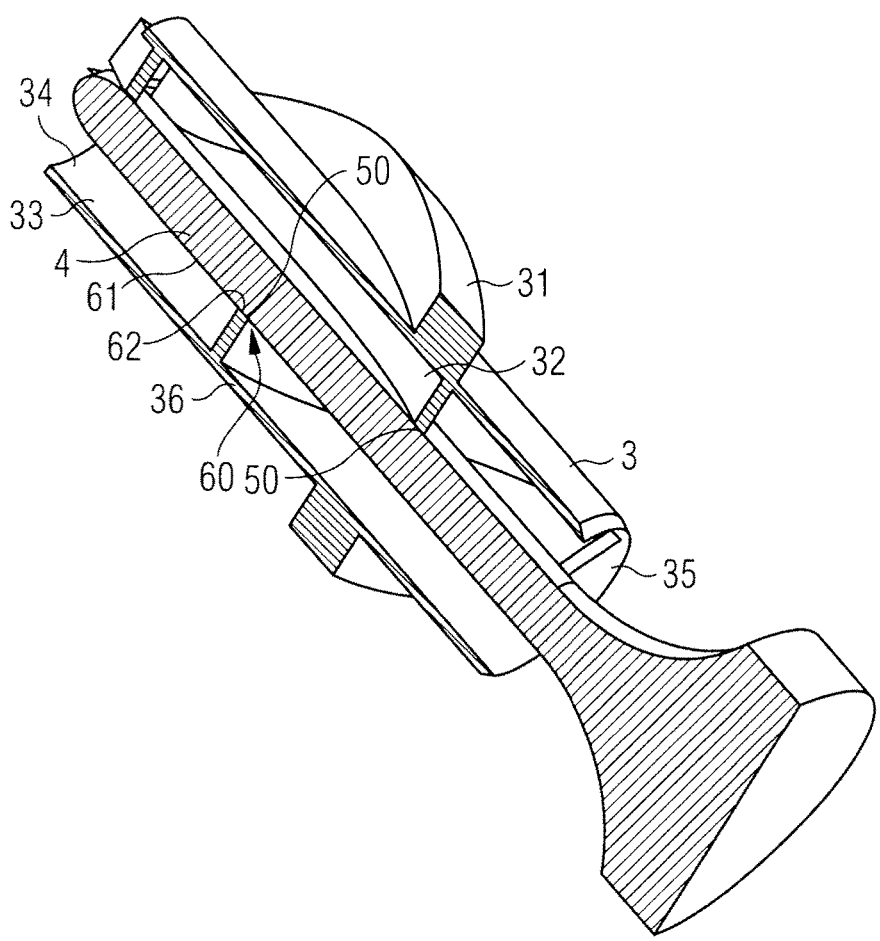
FIG. 6 shows a cross-sectional view of the impeller shown in FIG. 5.

Referring to FIGS. 1 and 2, a perspective and cross-sectional view of a blood pump 1 are respectively illustrated. The blood pump 1 comprises a pump casing 2 with a blood flow inlet 21 and a blood flow outlet 22. The blood pump 1 is designed as an intravascular pump, also called a catheter pump, and is deployed into a patient's blood vessel by means of a catheter 25. The blood flow inlet 21 is connected to a flexible cannula 23 which may be placed through a heart valve, such as the aortic valve, during use. The blood flow outlet 22 is placed in a side surface of the pump casing 2 and may be placed in a heart vessel, such as the aorta. The blood pump 1 is connected to the catheter 25 in order to supply the blood pump 1 with electric power to drive the pump 1 by means of a drive unit 5, as explained in more detail below. Generally, it will be appreciated that the flow in a blood pump may be in the reverse direction to that described in the present disclosure. For example, in the embodiment of FIG. 1, 22 may denote the blood flow inlet and 21 the blood flow outlet.

Referring to FIGS. 3 to 6, an impeller 3 is provided for conveying blood from the blood flow inlet 21 to the blood flow outlet 22 and is rotatably mounted about an axis of rotation within the pump casing 2. The axis of rotation is preferably the longitudinal axis of the impeller 3. The impeller 3 is rotatably supported by means of a bearing 60 formed of a pin 4 and a bearing structure inside the impeller 3, which therefore can be called a pin bearing. The bearing structure is formed by inner blades 32 as described in more detail below. Outer blades 31 are provided on a hub 36 of the impeller 3 for conveying blood once the impeller 3 rotates. Rotation of the impeller 3 is caused by the drive unit 5 arranged circumferentially about the pump casing 2. The drive unit 5 comprises a stator of an electric motor that creates a rotating magnetic field. Magnets in the outer blades 31 of the impeller 3 interact with the rotating magnetic field so as to cause rotation of the impeller 3 about the axis of rotation. It is also possible to form the outer blades 31 of a magnetic material. As can be seen in FIG. 2, the outer blades 31 are thicker than the inner blades 32 so as to provide enough space for magnets or magnetic material. The illustrated blood pump 1 is a mixed-type blood pump, wherein the major direction of flow is axial. It will be appreciated that the blood pump 1 could also be a purely axial blood pump, depending on the arrangement of the impeller 3, in particular the blades 31.

The impeller 3 includes a blood flow passage 33 that extends along the axis of rotation completely through the impeller 3. In this embodiment, the impeller 3 is hollow, i.e. the impeller hub 36 forms a cylindrical tube. The inner blades 32 are disposed in the passage 33. The pin 4 extends through the passage 33, with the pin 4 having a smaller diameter than the passage 33 so as to allow blood to flow past the pin 4. As also shown in FIGS. 3 to 6, exposed radially inner edges 50 of the inner blades 32 have a surface 62 facing radially inwards that engages or contacts an outer circumferential surface 61 of the pin 4 so as to form the bearing 60 that rotatably supports the impeller 3. In order to improve the bearing 60, in particular its hydrodynamic properties, the edges 50 of the inner blades 32 may be tapered in a circumferential direction.

Figure 7:
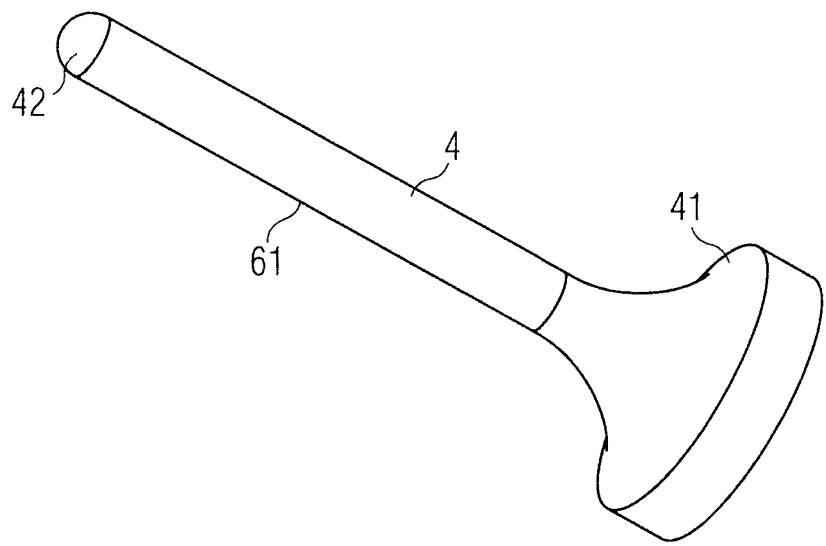
FIG. 7 shows a perspective view of the pin of the blood pump of FIG. 1.

The pin 4, i.e. the stationary bearing portion, is shown separately in FIG. 7. The pin 4 has a longitudinal body with a first axial end 41 and a second axial end 42. The first axial end 41 comprises an enlarged portion in order to fix the pin 4 in the pump casing 2, so that the pin 4 is stationary. As can be seen e.g. in FIG. 4, the enlarged portion 41 is formed to guide the blood flow towards the openings of the blood flow outlet 22. Instead of a single pin 4 that extends all the way through the impeller 3, two shorter pins may be provided that extend into first and second axial ends 34, 35 of the impeller 3, respectively. The outer circumferential surface 61 of the pin 4 provides the stationary bearing surface for the bearing 60.

Once rotation of the impeller 3 is caused by the drive unit 5, blood is pumped from the blood flow inlet 21 to the blood flow outlet 22 by means of the outer blades 31. At the same time, blood is conveyed through the passage 33 of the impeller 3 from the first axial end 34 to the second axial end 35 by means of the inner blades 32. In this embodiment, the blood flow through the passage 33 of the impeller 3 is directed in the same direction as the main blood flow from the blood flow inlet 21 to the blood flow outlet 22, i.e. the blood flow through the passage 33 is in a forward direction. The bearing 60 formed by the pin 4 and the inner blades 32 is cooled and actively washed out by the blood flow caused by the inner blades 32 to avoid blood clogging and clotting.

Figure 8:
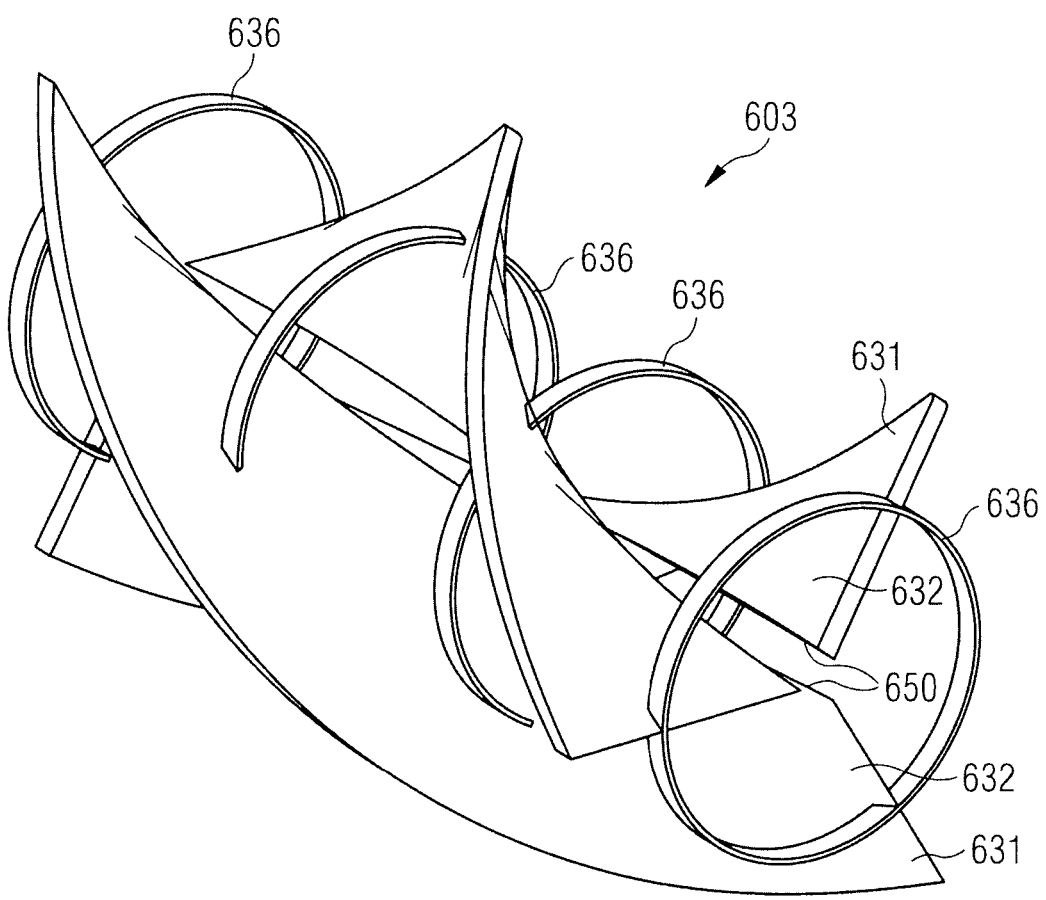
FIG. 8 shows a perspective view of an impeller arrangement of another embodiment.
Figure 9:
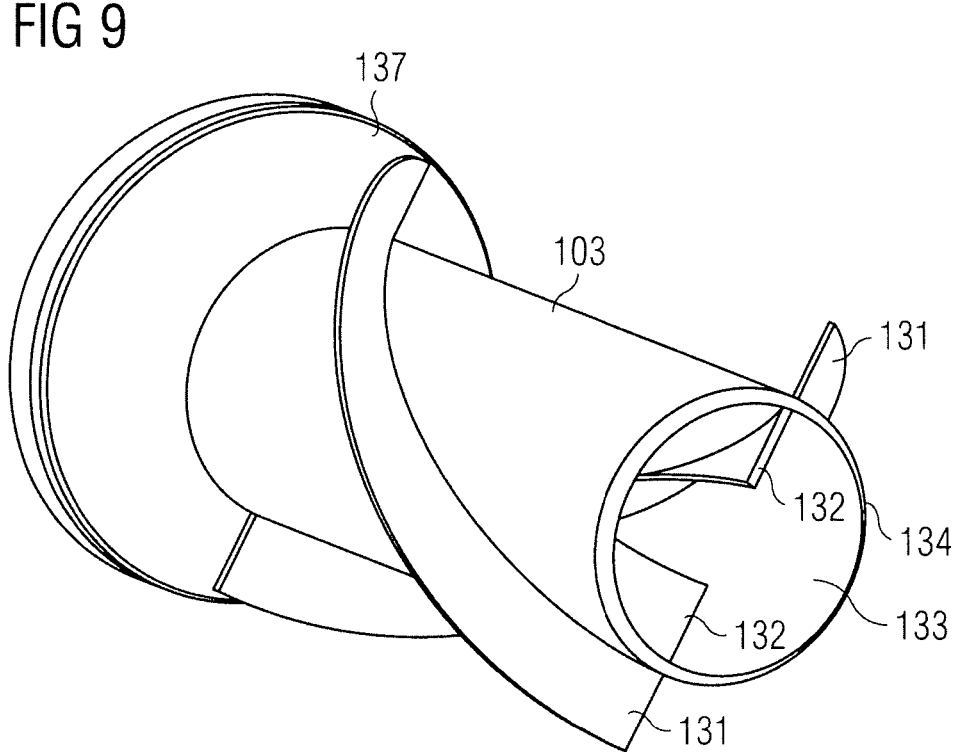
FIG. 9 shows a perspective view of an impeller arrangement of another embodiment.
Figure 10:
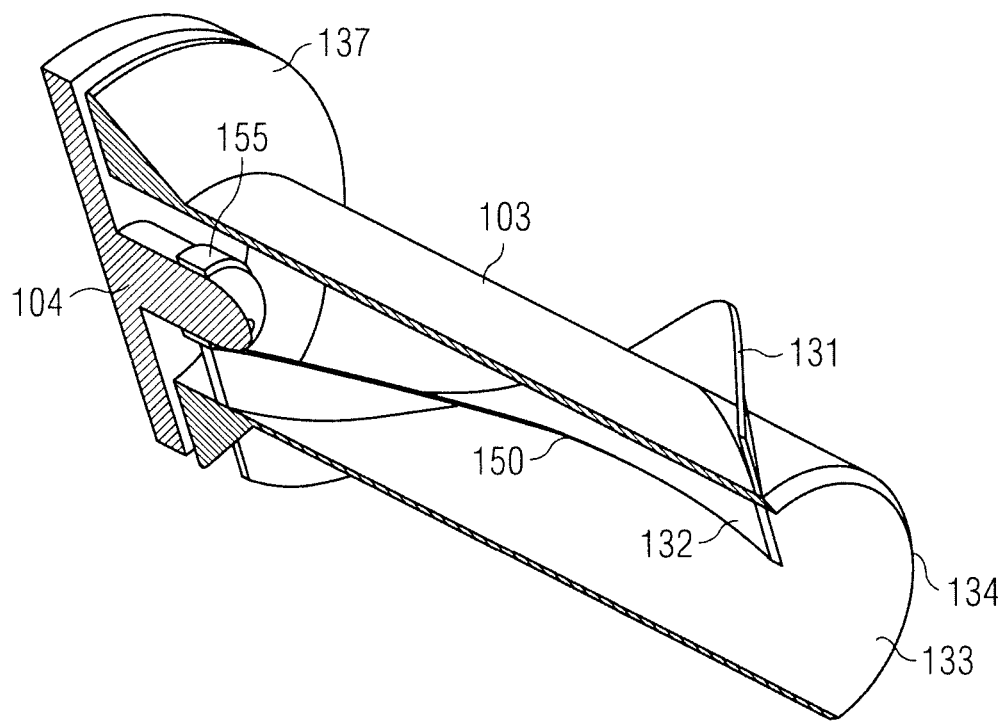
FIG. 10 shows a cross-sectional view of the impeller arrangement of FIG. 9.
Figure 11:
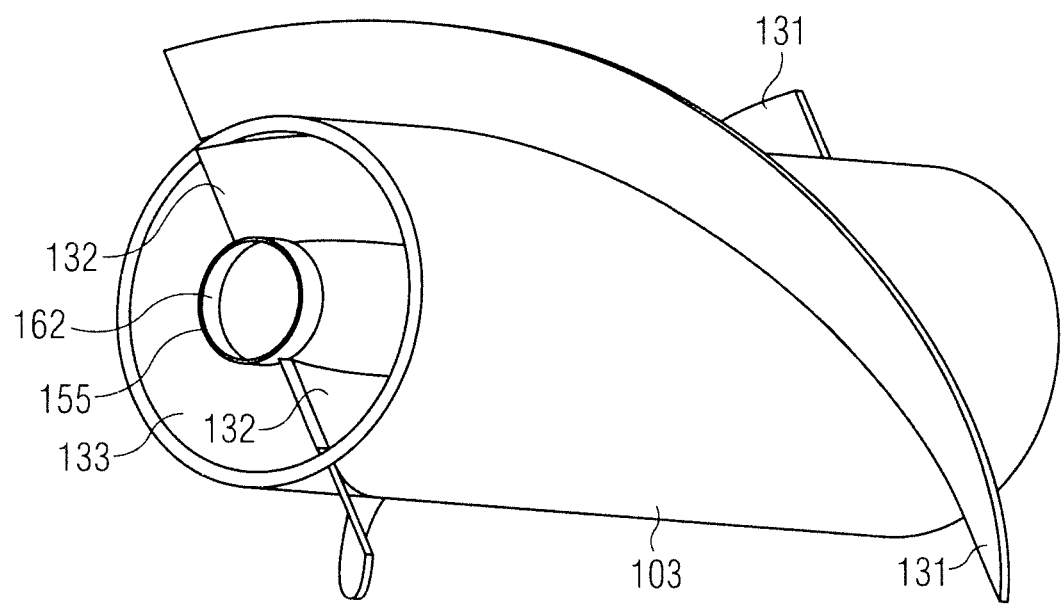
FIG. 11 shows a perspective view of the impeller of FIG. 9.
Figure 12:
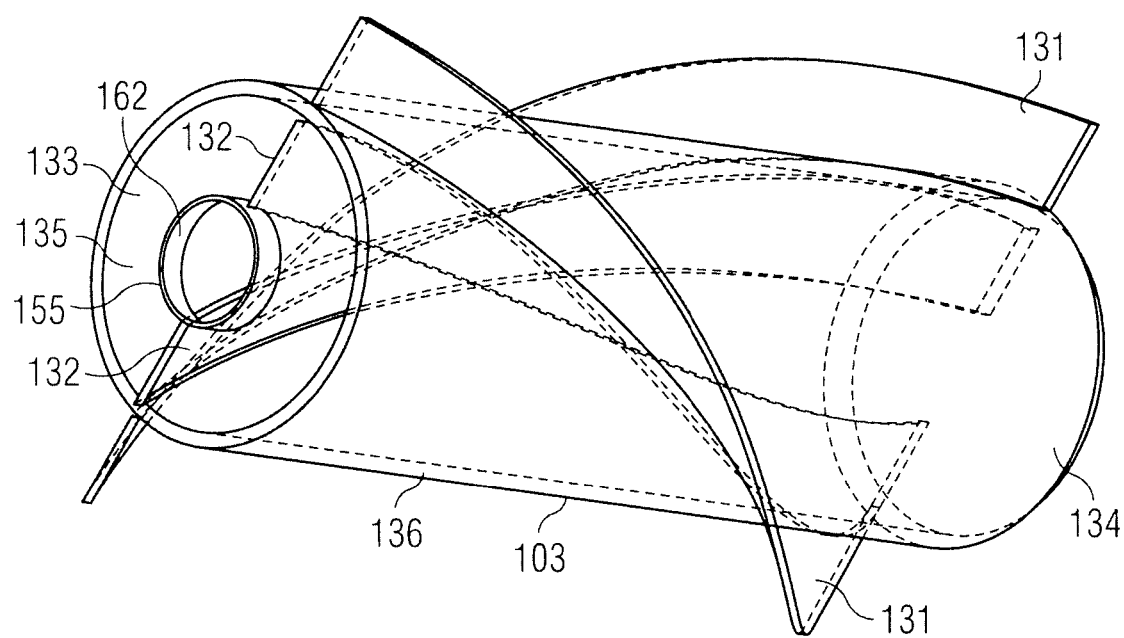
FIG. 12 shows a perspective and semi-transparent view of the impeller of FIG. 9.

Generally, it is important that the blood flow caused by the inner blades and the blood flow caused by the outer blades are hydraulically balanced so that both blade sets will cause a blood flow in a forward direction. This can be achieved by providing openings in the impeller hub so as to connect the blood flow passage with the environment of the impeller. FIG. 8 illustrates an embodiment of an impeller 603, wherein the hub 636 comprises a plurality of axially spaced rings that carry the blades. The blades are divided by the hub 636 into outer blades 631 and inner blades 632, where the exposed radially inner edges 650 of the inner blades form the rotating surface of the bearing as described in connection with the previous embodiment. The openings, i.e. the spaces between the rings 636, make it possible to achieve a hydraulic balance of the blood flows caused by the inner blades 632 and the outer blades 631, respectively. It will be appreciated that the openings can be designed in a different fashion. For example, there could be more or fewer rings, the axial dimensions of the rings and spaces between the rings could be larger or smaller as desired. The openings could also be formed as simple holes in the impeller hub that may assume any size and shape depending on the hydraulic requirements.

In FIGS. 9 to 13 is illustrated another embodiment, which corresponds to the embodiment shown in FIGS. 1 to 7 except for the design of the outer blades 131, the inner blades 132 and the pin 104. As can be seen in FIGS. 9 to 12, as in the embodiment of FIG. 8, the inner blades 132 are aligned with the outer blades 131, such that the inner blades 132 form a continuation of the outer blades 131 through the hub 136 of the impeller 103 or are mirrored at the hub 136. The inner blades 132 and outer blades 131 are separated by the hub 136 of the hollow impeller 3 and correspond to each other in size and shape. In this embodiment two inner blades 132 and two outer blades 131 are provided, with the outer blades 131 extending helically on the outer surface of the hub 136, and the inner blades 132 extending helically on the inner surface of the hub 136. The hub 136 is hollow and cylindrically shaped with a passage 133 extending from a first axial end 134 to a second axial end 135. A conical portion 137 is attached to the second axial end 135 to guide the blood flow towards the blood flow outlet 22 of the blood pump 1.

Figure 13:
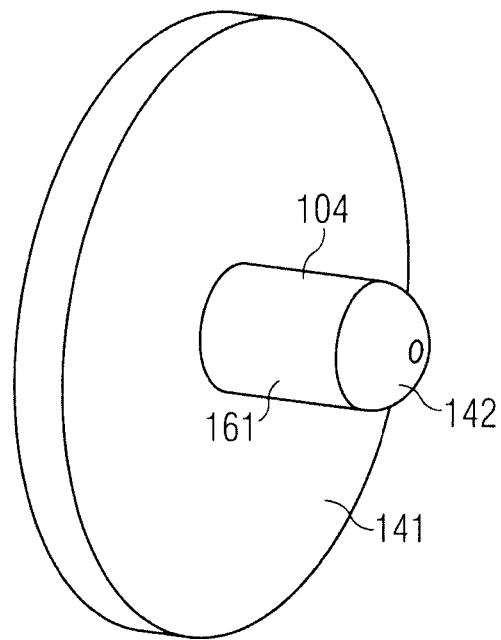
FIG. 13 shows a perspective view of the pin of the impeller arrangement of FIG. 9.

In this embodiment, a ring 155 is attached to the inner blades 132 to provide a rotating bearing surface 162 that engages the pin 104, in particular an outer surface 161 of the pin 104, to form the bearing 160. The ring 155 provides radial centering of the impeller 103 and guides rotation of the impeller 103 about the axis of rotation. The pin 104 is shown in FIG. 13 and is shorter than in the previously described embodiment. It has a first axial end 141 comprising a plate to fix the pin 104 in the pump casing, and a second axial end 142. It will be appreciated that the impeller 103 shown in FIGS. 9 to 12 may also be used with the long pin 4 shown in FIG. 7. The ring 155 may provide the only bearing surface. However, in particular when the impeller 103 is used with a longer pin, there may be two or more rings arranged along the length of the impeller 103, e.g. one ring at each of the first and second axial ends 134, 135. In the latter case, it may also be possible to provide two of the short pins 104, with one of the pins being located at the first axial end 134 of the impeller 103 and the other pin being located at the second axial end 135 thereof. In both cases, the mating area of the bearing can be confined to a minimum.

Figure 14:
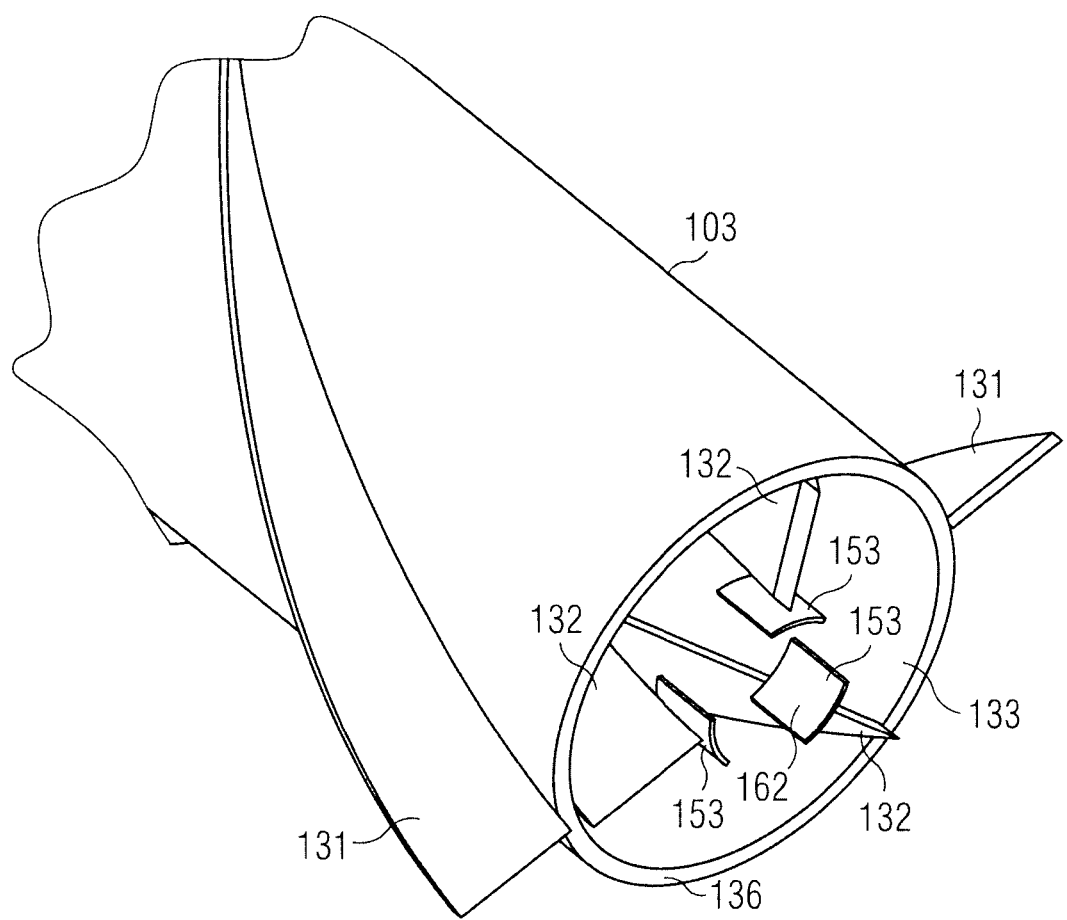
FIG. 14 shows a perspective view of an impeller according to another embodiment.
Figure 15:
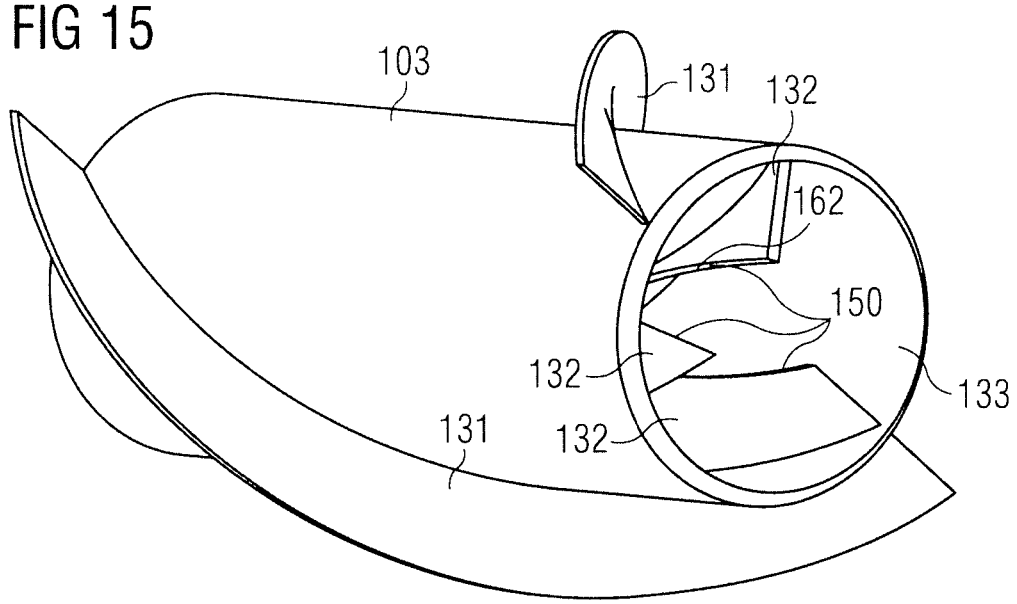
FIG. 15 shows a perspective view of an impeller according to another embodiment.

FIG. 14 illustrates another embodiment, wherein wings 153 are attached to the inner blades 132 to define bearing surfaces 162. This embodiment is similar to the embodiment wherein the ring 155 defines the rotating bearing surface 162. The separate wings 153 may improve flushing of the bearing 160 compared to a closed ring. In FIG. 15 is shown another embodiment, wherein the impeller 103 does not have any additional bearing surfaces, but wherein the rotating bearing surfaces 162 are defined by the radially inner edges 150 of the inner blades 132 as in the embodiment of FIGS. 1 to 7. In the other embodiments as well, exposed radially inner edges 150 of the inner blades 132 may function as rotating bearing surfaces, in addition to the bearing surfaces 162 formed by the ring 155 or wings 153. The size and shape of one or more pins will then be chosen such that the radial inner edges 150 of the inner blades 132 engage the pin or pins. It will be further appreciated that the number of inner blades 132 can differ from the number of outer blades 131 to match the hydraulic performance of both blades.

Figure 16:
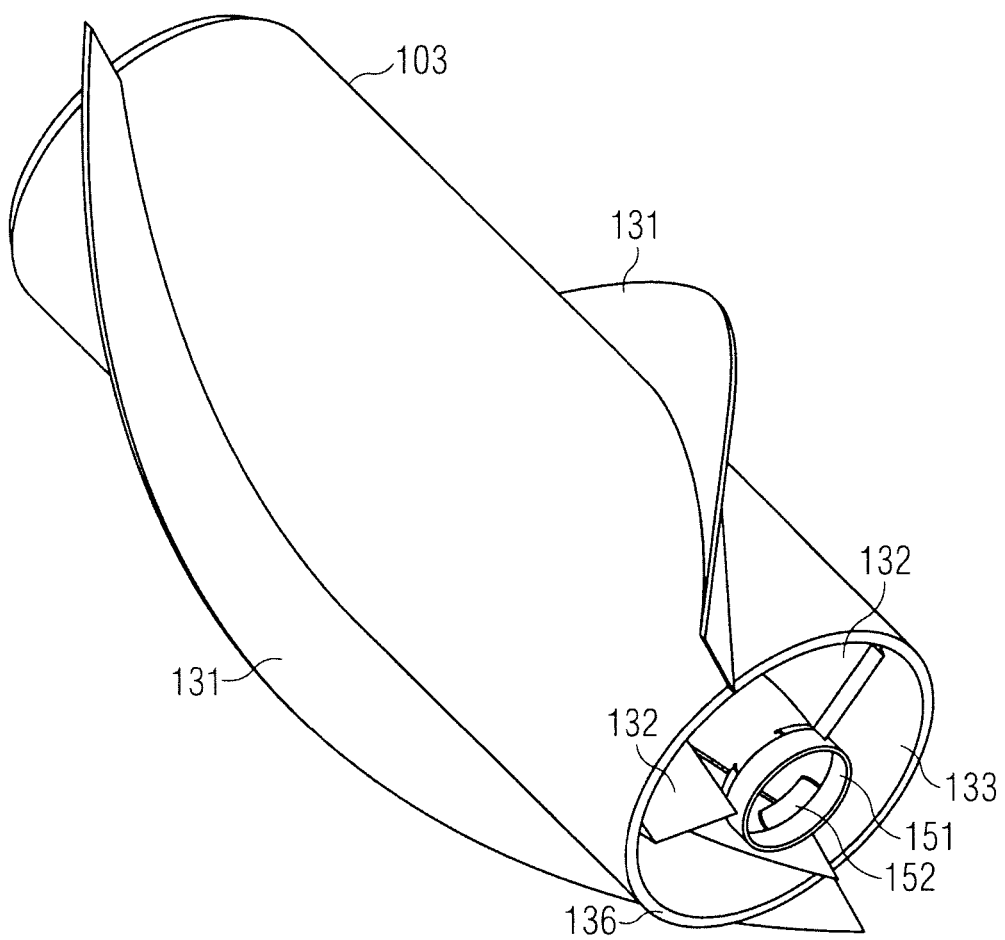
FIG. 16 shows a perspective view of an impeller according to another embodiment.
Figure 17:
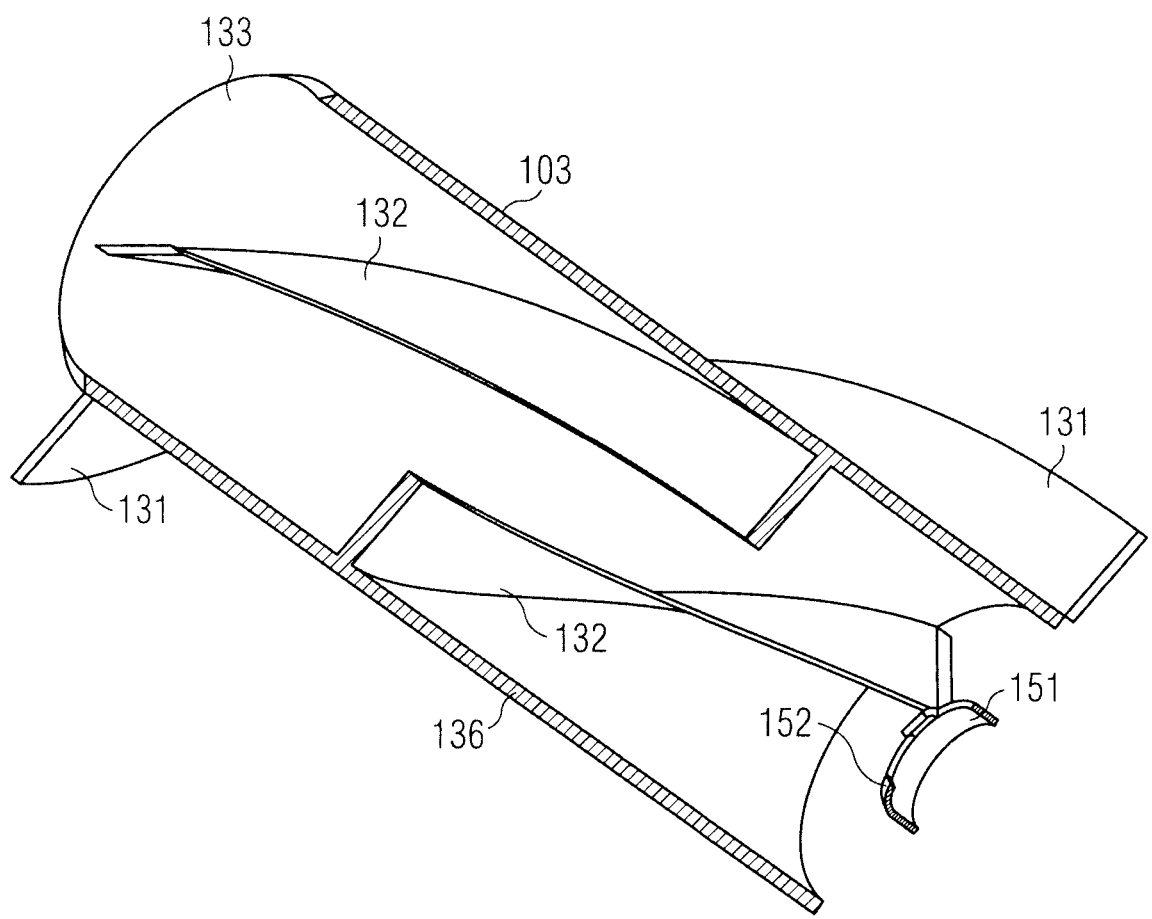
FIG. 17 shows a cross-sectional view of the impeller of FIG. 16.
Figure 18:
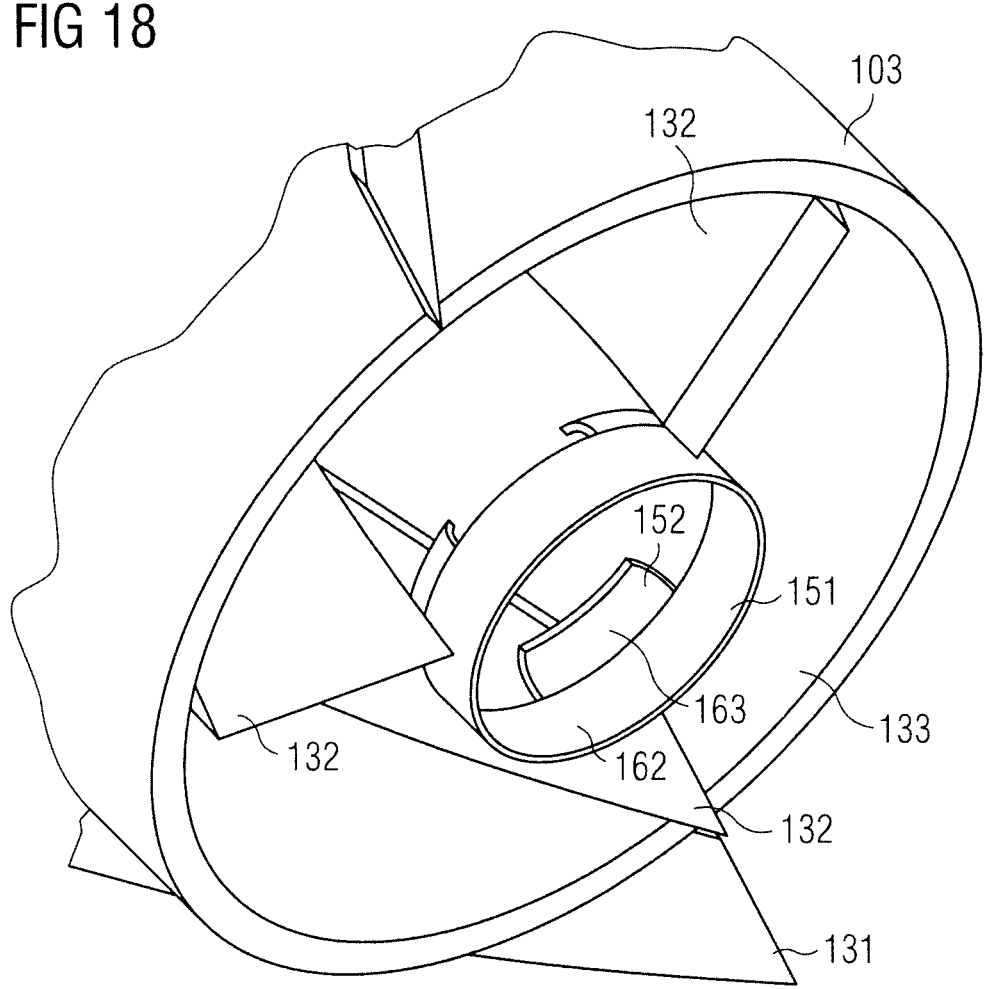
FIG. 18 shows an enlarged cross-sectional view of the impeller of FIG. 16.

In FIGS. 16 to 18 is illustrated another embodiment, wherein the bearing structure comprises a ring-shaped portion 151 as well as curved protrusions 152 forming additional bearing surfaces 163 that are sized and shaped to conform to the size and shape of the axial end 142 of the pin 104. In particular, the protrusions 152 may form a hemispherical shape that corresponds to the hemispherical end 142 of the pin 104. It will be appreciated that the protrusions 152 may be connected to form a closed surface that engages the pin 104. Likewise, the shape of the protrusions 152 and the end 142 of the pin 104 does not necessarily have to be hemispherical, but may be e.g. conical. In this embodiment, the bearing also provides axial support of the impeller 103, not only radial centering. Apart from that, in this embodiment the number of inner blades 132 is different from the number of outer blades 131. Three inner blades 132 are disposed in the passage 133 of the impeller 103, while only two outer blades 131 are provided on the outer surface of the hub 136.

Figure 19:
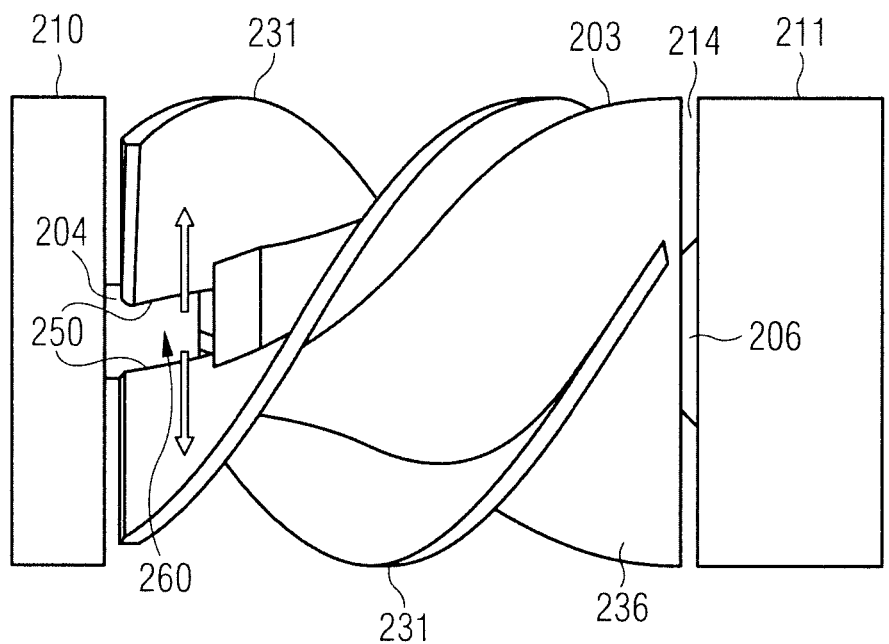
FIG. 19 shows a side elevation view of an impeller assembly according to another embodiment.
Figure 20:
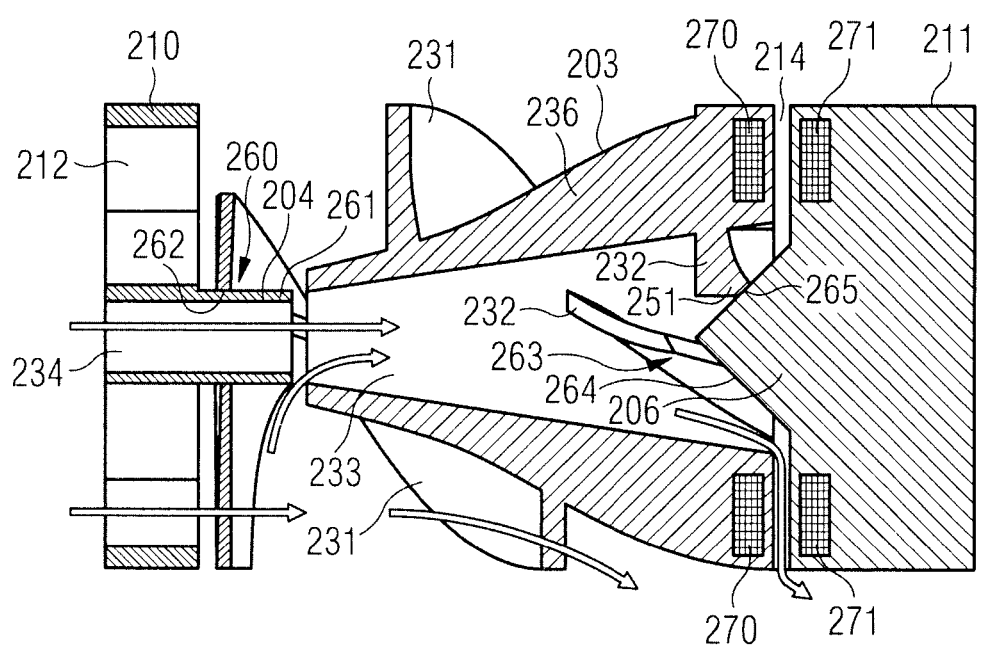
FIG. 20 shows a cross-sectional view of the assembly of FIG. 19.
Figure 21:
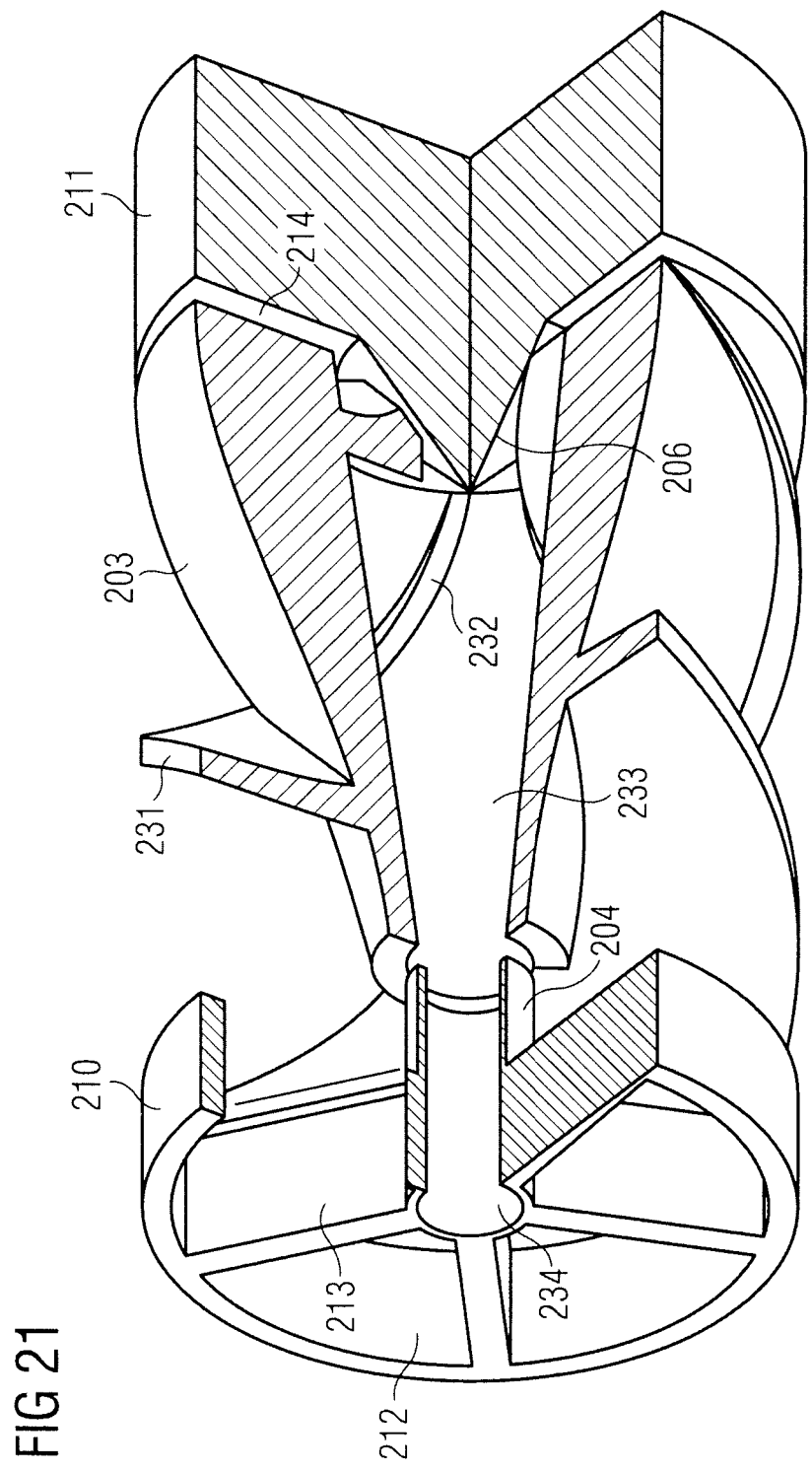
FIG. 21 shows a perspective cross-sectional view of the assembly of FIG. 19.

Referring to FIGS. 19 to 21, an impeller assembly according to another embodiment is illustrated, which can be employed in a blood pump similar to the blood pump shown in FIG. 1. In particular, the impeller assembly can be used in an intravascular catheter pump and arranged in a pump casing connected to a catheter as shown and described in connection with FIG. 1. The impeller assembly of FIGS. 19 to 21 comprises an impeller 203 having a set of outer blades 231 for conveying blood from a blood flow inlet to a blood flow outlet of the blood pump. The impeller 203 further has a blood flow passage 233 axially extending through the impeller 203. A set of inner blades 232 is disposed in the blood flow passage 233 in a downstream end portion of the passage 233. In this embodiment, the impeller 203 has a tapered shape such that a blood flow (indicated by arrows)

is guided radially outwards. The blood flow passage 233 is also tapered and increases in diameter towards the downstream end. However, any other shape, such as cylindrical, would be suitable for the blood flow passage 233.

The impeller 203 is supported by two bearings 260, 263, one at the upstream end and one at the downstream end of the impeller 203. In the downstream bearing 263, a stationary bearing portion 211 that is configured to be coupled to the pump casing is provided. The stationary bearing portion 211 comprises a conical protrusion 206 that extends into the blood flow passage 233 of the impeller 203 and interacts with the inner blades 232 to form the bearing 263. More specifically, exposed radially inner edges 251 of the inner blades 232 interact with the cone 206. The exposed radially inner edges 251 define rotating bearing surfaces 265 that engage a stationary bearing surface 264 of the cone 206. Due to the conical shape of the stationary bearing portion, the bearing 263 provides axial and radial support for the impeller 203. At the same time, the inner blades 232 actively pump blood towards the bearing 263 (indicated by arrows), in particular along the bearing surfaces 264, 265 to wash out and cool the bearing 263. This blood flow through the blood flow passage 233 of the impeller 203 exits the passage 233 at a downstream end through a gap 214 between the impeller 203 and the stationary bearing portion 211 to join the main blood flow.

At its upstream end, the impeller 203 is supported by another bearing 260. A stationary bearing portion 210 is provided that can be coupled to the pump casing. As best shown in FIG. 21, the stationary bearing portion 210 is ring-shaped and comprises a plurality of apertures 212 that allow blood to enter the impeller region. The apertures 212 may have any suitable number and design allowing blood to pass therethrough. In the present embodiment, the apertures 212 are defined by a plurality of struts 213. Any number of struts 213 can be chosen, such as at least two, three, four or five. The struts 213 support a pin 204 extending along the axis of rotation towards the impeller 203. The pin 204 defines a stationary bearing surface 261 that interacts with a rotating bearing surface 262 defined on exposed radially inner edges 250 of the outer blades 231. In order to form exposed radially inner edges 250 on the outer blades 231, the outer blades 231 extend beyond the hub 236 of the impeller 203. That is to say, the outer blades 231 have an axial end portion that protrudes beyond the impeller hub 236. In the present case, all of the three outer blades 231 extend beyond the hub 236 substantially the same distance to form the exposed radially inner edges 250 that engage the pin 204. However, it may be sufficient if not all outer blades 231 form exposed radially inner edges. This type of bearing provides an open design, where the bearing surfaces 261, 262 are in contact with blood. The bearing surfaces 261, 261 are effectively washed out and cooled. Washing of the bearing surfaces 261, 262 upon rotation of the blades 231 is illustrated by arrows in FIG. 19. The mere fact of the blades 231 being put in rotation causes blood deposit to be centrifuged from the bearing 260 in a radially outward direction. This wash-out flow is independent of the primary blood flow caused by the blades 231.

As can be seen in FIGS. 20 and 21, the pin 204 has an axial passage 234 that allows blood to flow therethrough. In particular, the passage 234 of the pin 204 is aligned with the blood flow passage 233 of the impeller 203, which facilitates blood to enter the passage 233 of the impeller 203 and increases blood flow volume through the impeller 203 to provide effective active wash-out of the bearing 263 as described above. Blood will also enter the blood flow passage 233 from between the outer surface of the pin 204 and the distal end of the impeller 203 (indicated by arrows in FIG. 20).

The impeller 203 can be further adjusted or also driven by an arrangement including magnets or electromagnets 270, 271 as schematically shown in FIG. 20. Magnets 271 in the stationary bearing portion 211 interact with magnets 270 in the impeller 203 to form a magnetic coupling. The magnets 270, 271 can be arranged to cause an attractive or repulsive magnetic force to support axial alignment of the impeller 203. It will be appreciated that any suitable drive can be used to cause rotation of the impeller 203 about the axis of rotation. For example, the magnets 270 in the impeller 203 can interact with a rotating magnetic field that is caused either by an electrical unit in the stationary bearing portion 211, i.e. axial, or by an electrical unit surrounding the impeller, i.e. radial. Alternatively, the magnets 271 may be permanent magnets and may be part of a rotating disc, rotatably sealed against the blood.

Figure 22:
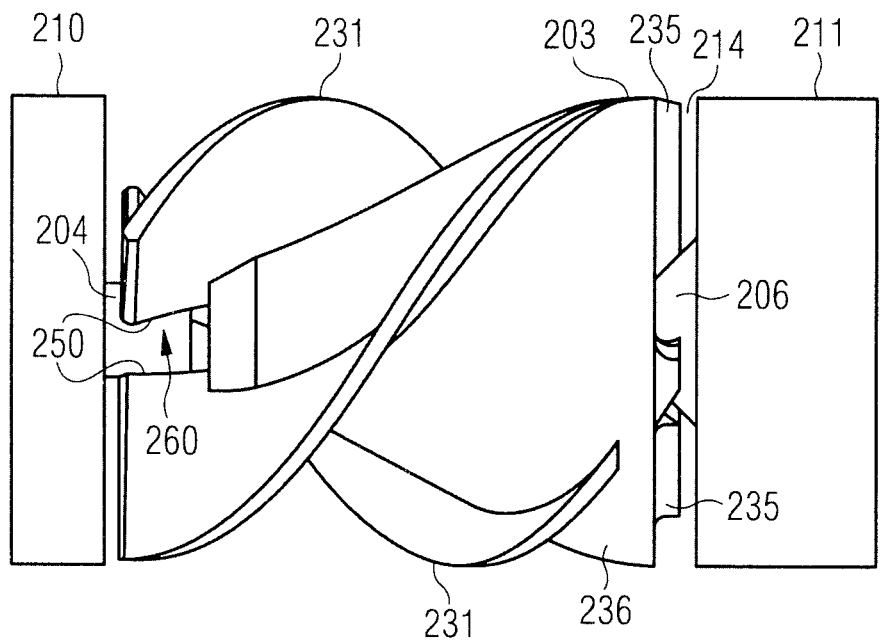
FIG. 22 shows a side elevation view of an impeller assembly according to another embodiment.
Figure 23:
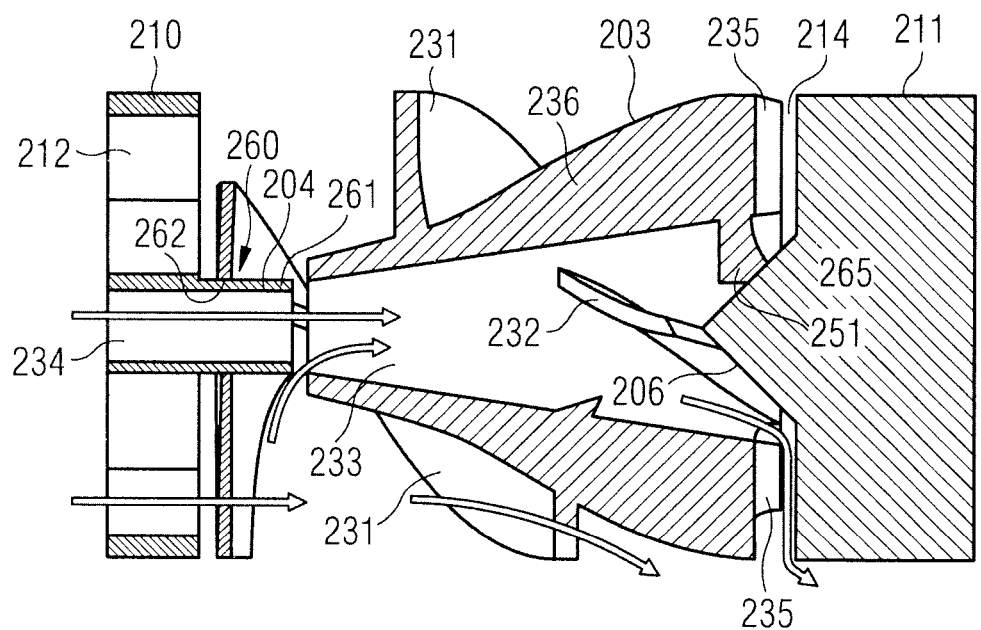
FIG. 23 shows a cross-sectional view of the assembly of FIG. 22.
Figure 24:
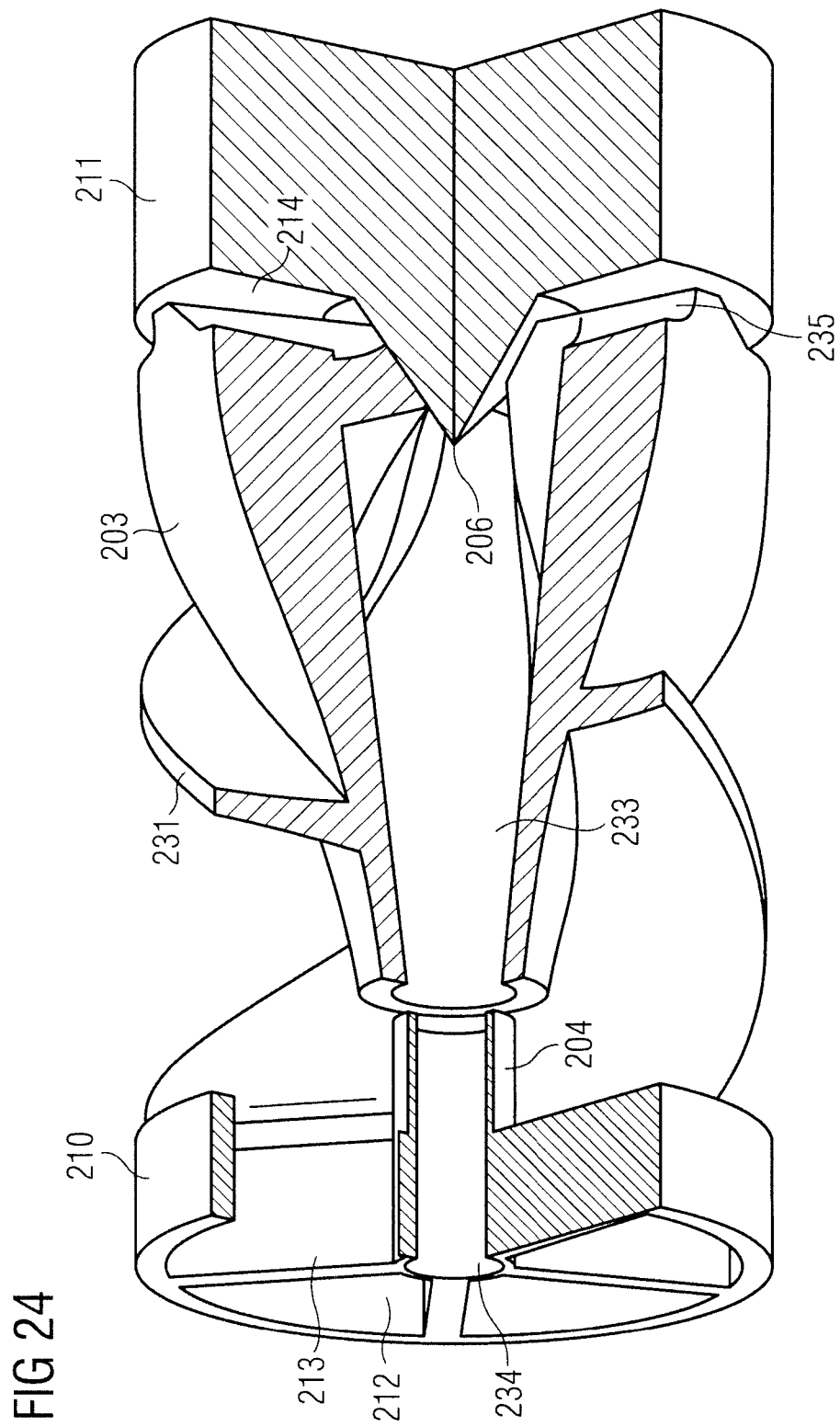
FIG. 24 shows a perspective cross-sectional view of the assembly of FIG. 22.

Another embodiment of an impeller assembly which is substantially identical to the embodiment shown in FIGS. 19 to 21 is shown in FIGS. 22 to 24. The only difference is that secondary blades 235 are provided at the downstream end surface of the impeller 203 in the gap 214. This enhances blood flow through the gap 214 to wash out the gap 214. Furthermore, the secondary blades 235 provide an axial hydrodynamic bearing as they interact with a surface of the stationary bearing portion 211.

Figure 25:
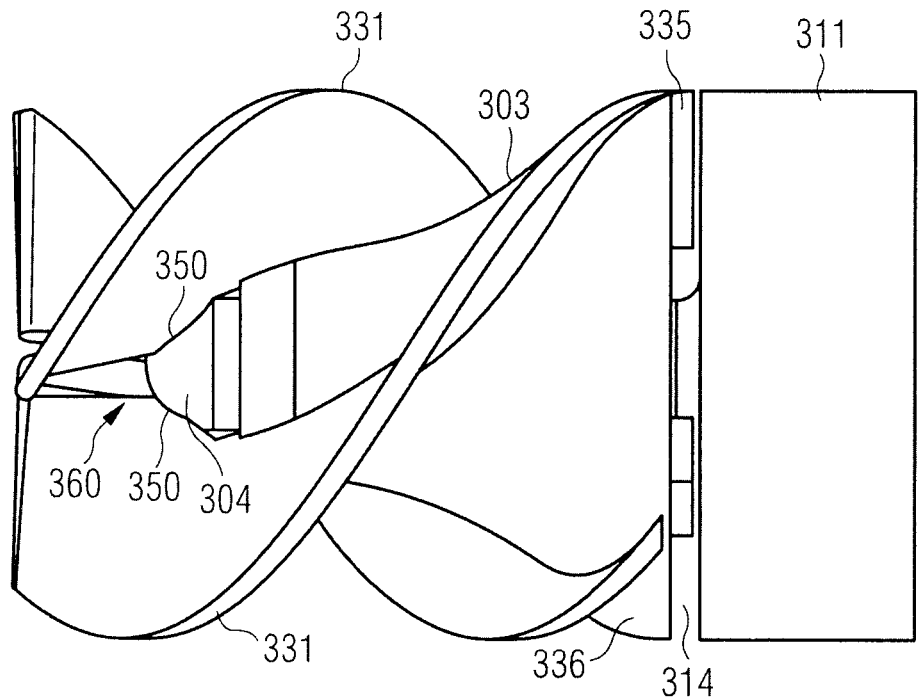
FIG. 25 shows a side elevation view of an impeller assembly according to another embodiment.
Figure 26:
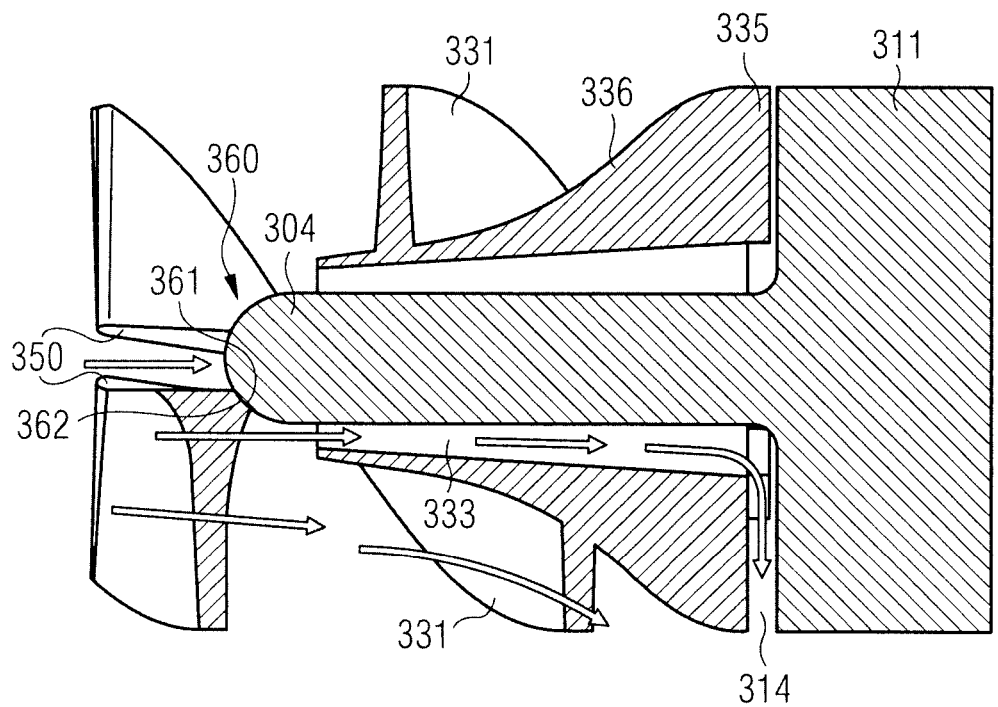
FIG. 26 shows a cross-sectional view of the assembly of FIG. 25.
Figure 27:
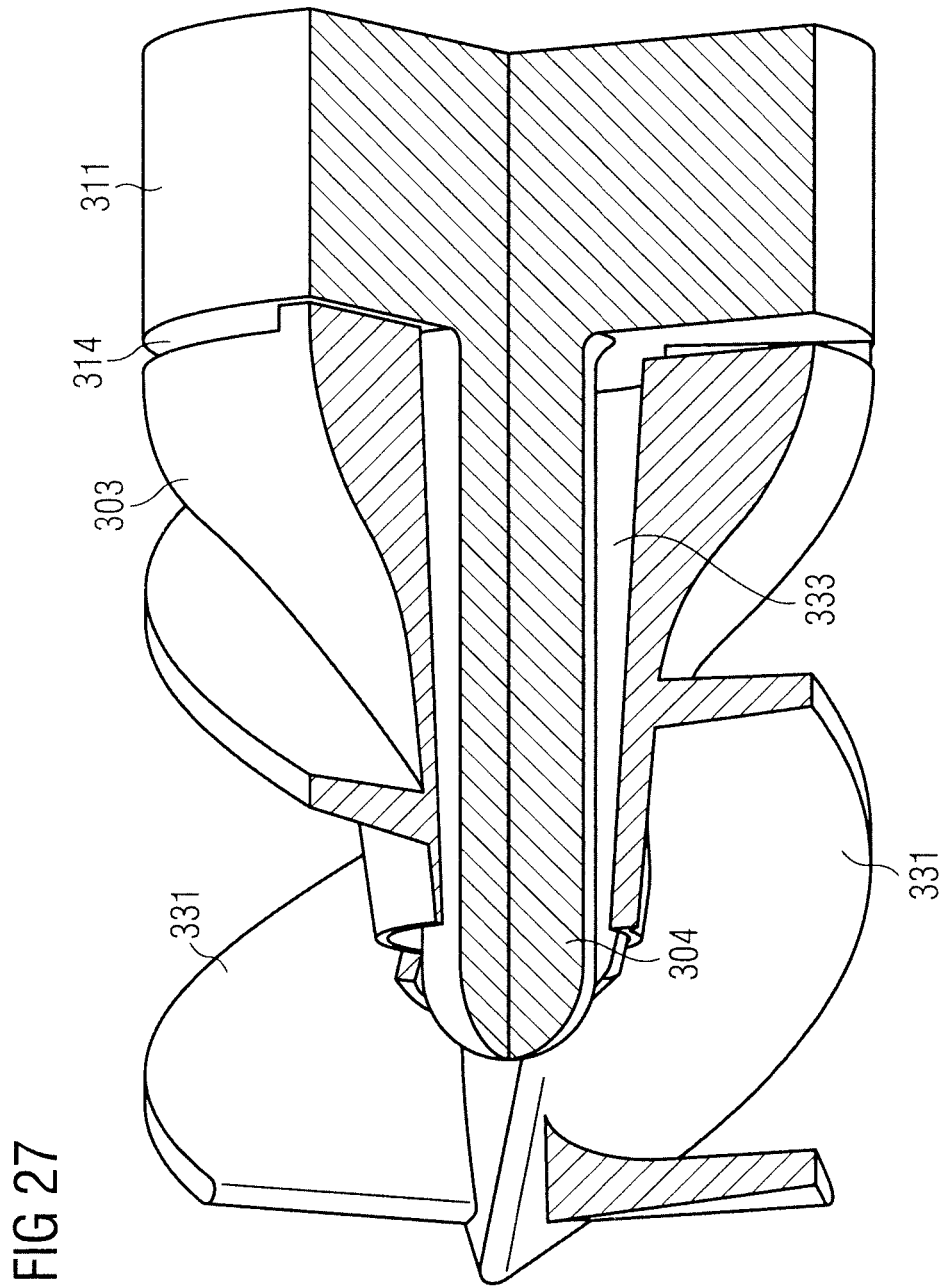
FIG. 27 shows a perspective cross-sectional view of the assembly of FIG. 25.

Referring to FIGS. 25 to 27, another embodiment of an impeller assembly is illustrated. In this embodiment, the impeller 303 only has outer blades 331 but no inner blades. Nevertheless, inner blades could also be provided in this embodiment that act like the inner blades described in connection with the embodiment shown in FIGS. 1 to 7. The impeller 303 is supported by a bearing 360 comprising a stationary bearing portion 311 having a pin 304. The pin 304 extends completely through a blood flow passage 333 of the impeller 303. The blood flow passage 333 has a larger diameter than the pin 304 so as to allow blood to flow past the pin 304 through the passage 333 and through a gap 314 at an axial end surface of the impeller 303. Secondary blades 335 are provided to enhance blood flow through the gap 314 and to provide a hydrodynamic bearing. It will be appreciated, however, that the secondary blades 335 can be omitted.

As in the previous embodiment, the outer blades 331 are disposed on an outer surface of the hub 336 of the impeller 303 and axially extend beyond the hub 236 so as to form exposed radially inner edges 350 and to define rotating bearing surfaces 362. The rotating bearing surfaces 362 engage a stationary bearing surface 361 defined by an axial end of the pin 304 that protrudes from the passage 333 of the impeller 303. In this manner, a bearing 360 is provided that axially and radially supports the impeller 303. The larger diameter of the impeller passage 333 may allow a certain amount of pivoting of the impeller 303, which can be balanced by the hydrodynamic bearing formed by the secondary blades 335. The blades 331 as illustrated do not meet at the axis of rotation to form an open bearing 360 where blood can enter the bearing 360 in an axial direction (indicated by an arrow) to flush the bearing surfaces 361, 362. They may also meet at the axis of rotation, still allowing blood to enter the bearing 360 in an axial direction.

Figure 28:
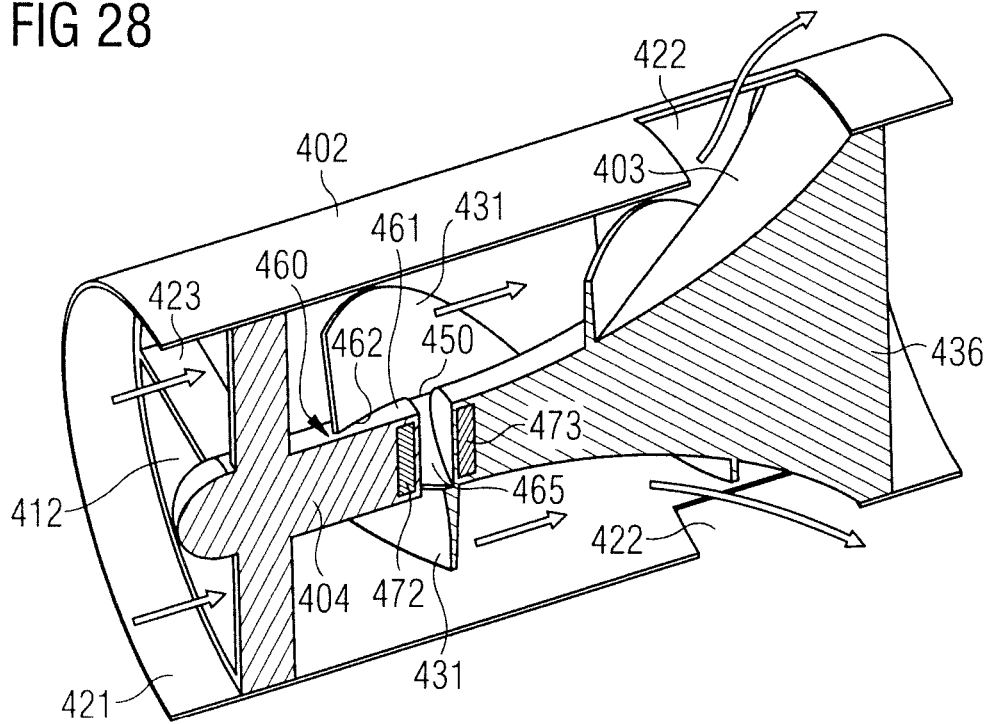
FIG. 28 shows a cross-sectional view of an impeller assembly according to another embodiment.
Figure 29:
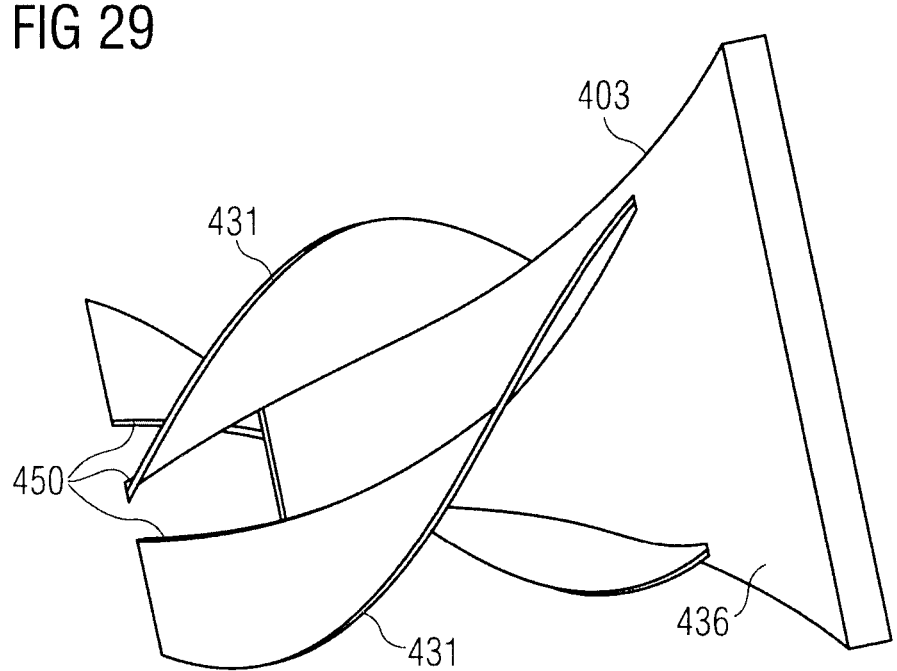
FIG. 29 shows a perspective view of the impeller of FIG. 28.
Figure 30:
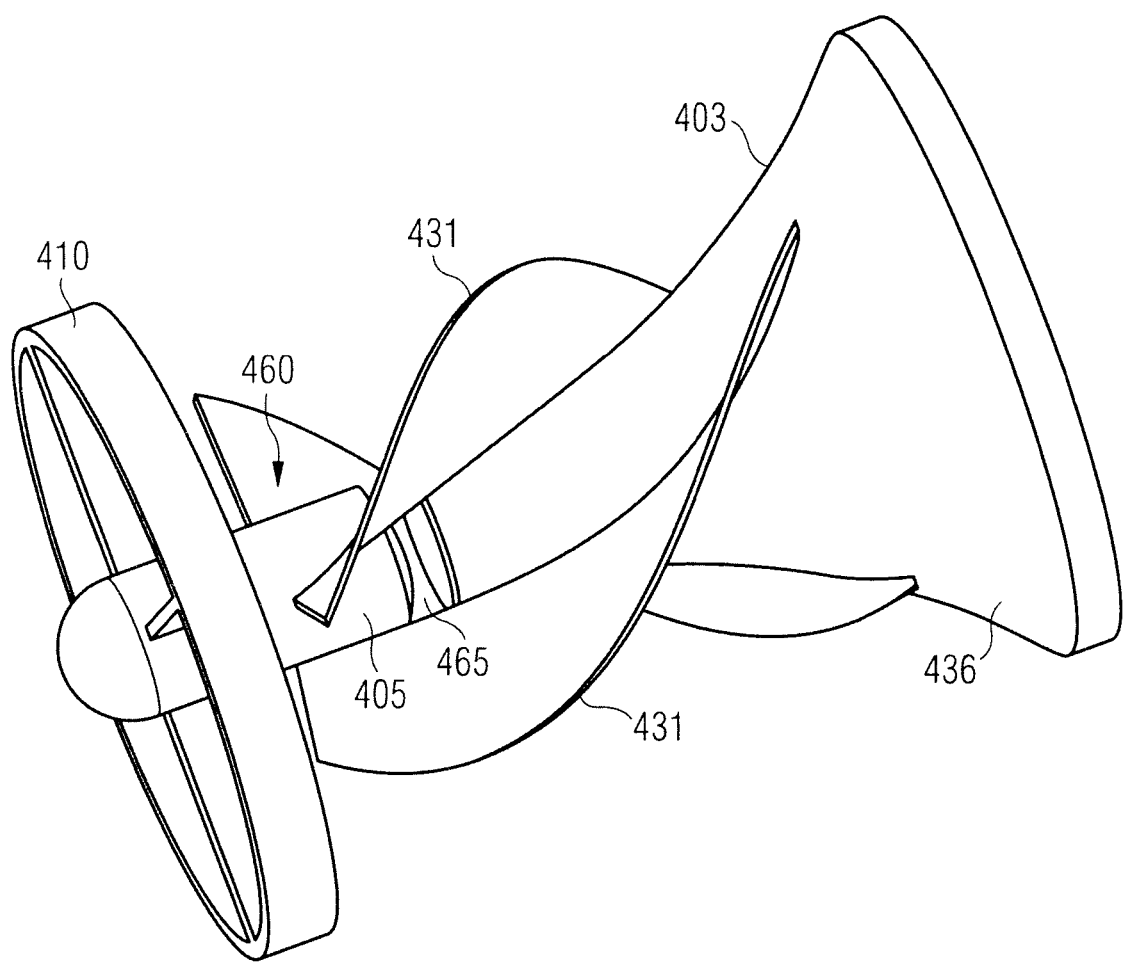
FIG. 30 shows a perspective view of the impeller along with the stationary bearing portion of FIG. 28.

Another embodiment of an impeller assembly is illustrated in FIGS. 28 to 30. It is similar to that of FIGS. 19 to 21 but does not include a blood flow passage through the impeller. FIG. 28 shows a cross-section through the impeller 403 disposed in a pump casing 402 having a blood flow inlet 421 and a blood flow outlet 422. The blood flow inlet 421 is disposed at an axial end of the pump casing 402 while the blood flow outlet 422 is radially disposed about the pump casing 402. This is similar to the embodiment shown in FIGS. 1 to 7. Therefore, there can also be provided in this embodiment a flexible cannula at the inlet end and a catheter at the opposing end, as described in detail above. Likewise, there can be provided an axial drive unit at the downstream end of the impeller 403 (not shown).

The impeller 403 comprises a set of outer blades 431 that axially protrude from the hub 436 of the impeller 403 so as to define exposed radially inner edges 450. The impeller 403 is supported by a bearing 460 that is formed by rotating bearing surfaces 462 on the exposed radially inner edges 450 of the blades 431 and a stationary bearing surface 461 on a pin 404 of a stationary bearing portion 410. The stationary bearing portion 410 comprises apertures 412 defined by struts 413 so as to allow blood to enter the impeller region. As in the previous embodiment, an axial passage through the pin 404 could be provided such that blood can enter the gap 465 between the impeller 403 and the pin 404 to improve wash-out of the gap 465. In order to avoid contact between the impeller 403 and the pin 404 in the region of the gap 465, permanent magnets 472, 473 are provided in the impeller 403 and the pin 404, respectively, to cause a repulsive magnetic force. It will be appreciated that this magnet arrangement could be employed in any of the disclosed embodiments or could be omitted. In the case of the other arrangements, the magnets may be ring magnets allowing for blood to flow through the center along the axis of rotation.

Figure 31:
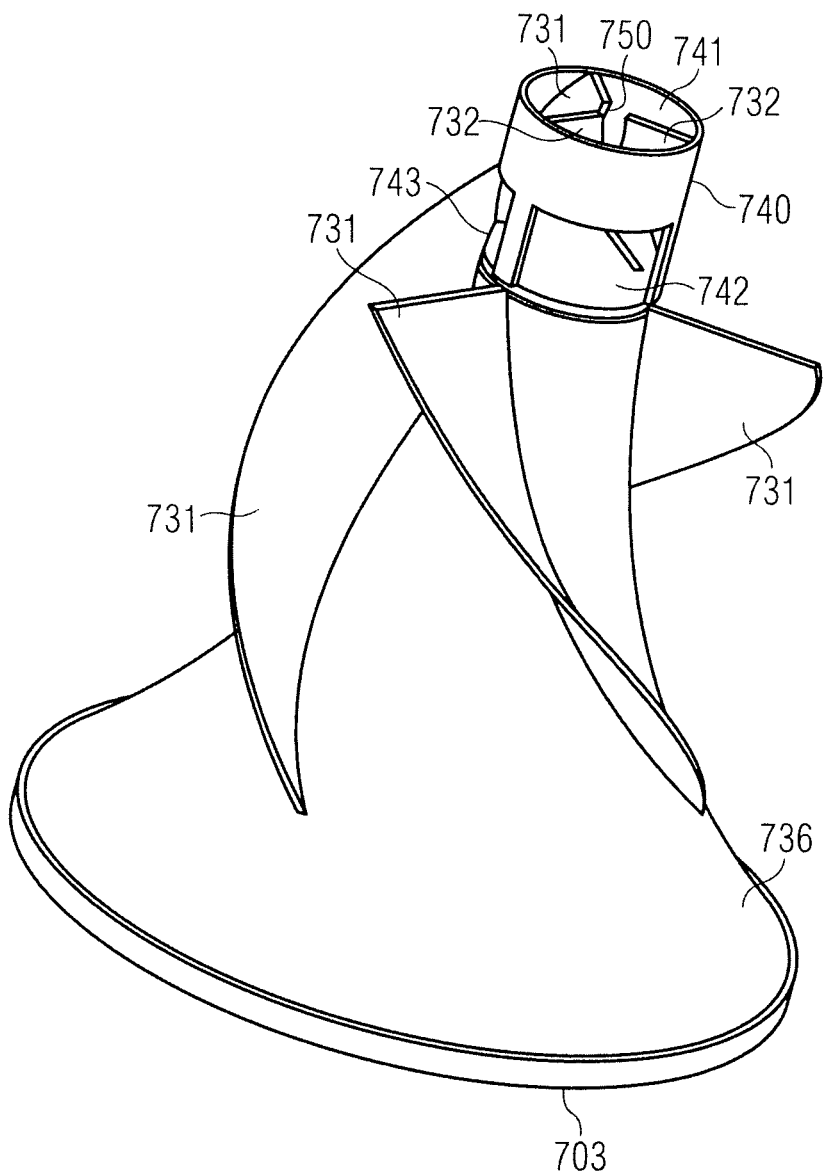
FIG. 31 shows a cross-sectional view of an impeller according to another embodiment.

Referring to FIG. 31, another embodiment of an impeller 703 is shown. As in the previous embodiments, the impeller 703 has a tapered hub 736 with a set of outer blades 731 on the outer surface of the hub 736 for causing the main blood flow. However, the blades 731 do not extend axially beyond the impeller hub 736. Instead, secondary blades 732 are provided at a tip 743 of the impeller 703. The secondary blades 732 are smaller than the primary blades 731 and form exposed radially inner edges 750 that are configured to engage a pin to form an open bearing as described in connection with the previous embodiments. A shroud 740 is provided that surrounds and connects the secondary blades 732 such that blood can flow from an inlet 741 to an outlet 742. Blood does not flow through the impeller hub 736 but only along the secondary blades 732.

Figure 32:
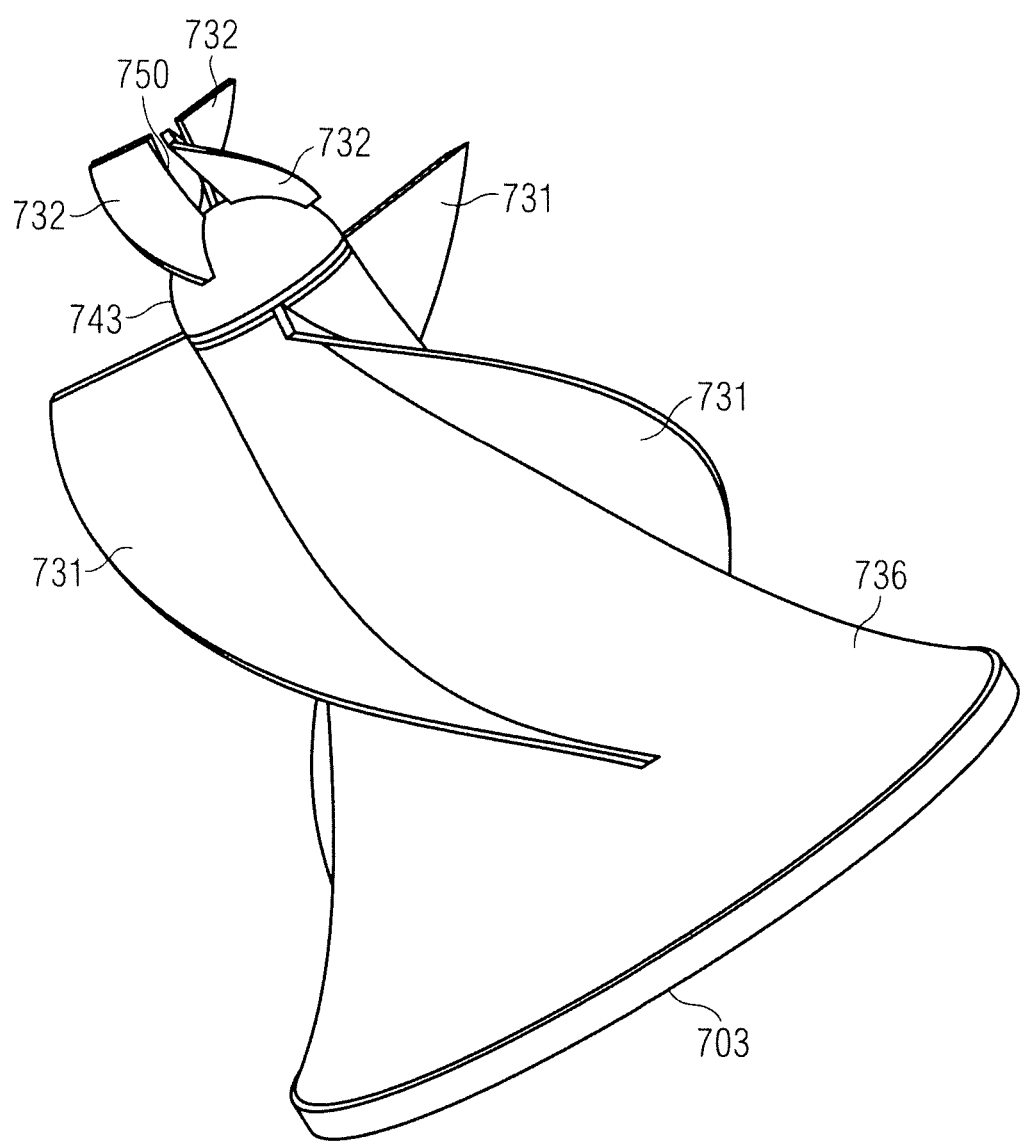
FIG. 32 shows a cross-sectional view of an impeller according to another embodiment.
Figure 33:
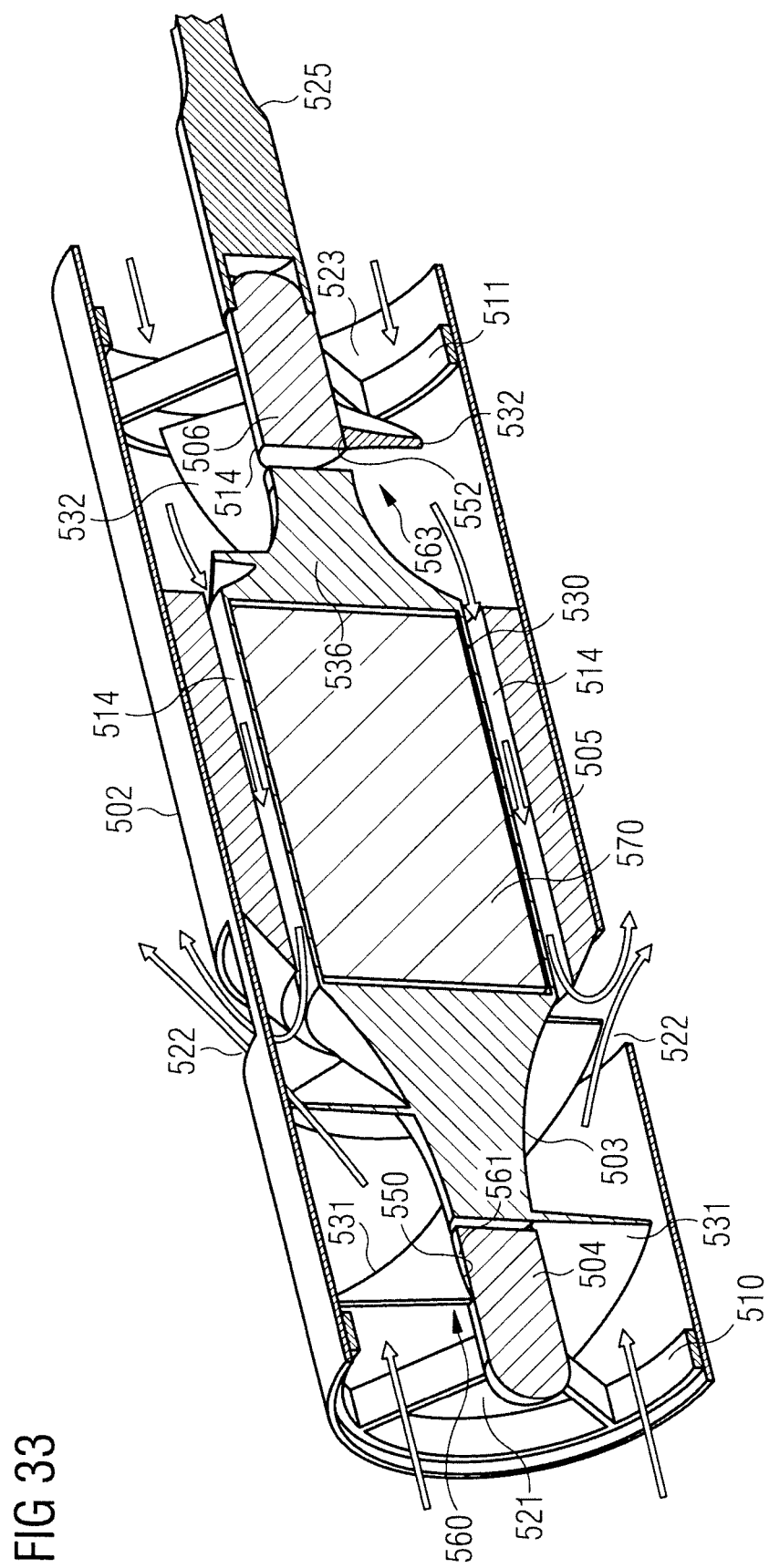
FIG. 33 shows a cross-sectional view of a blood pump according to another embodiment.
Figure 34:
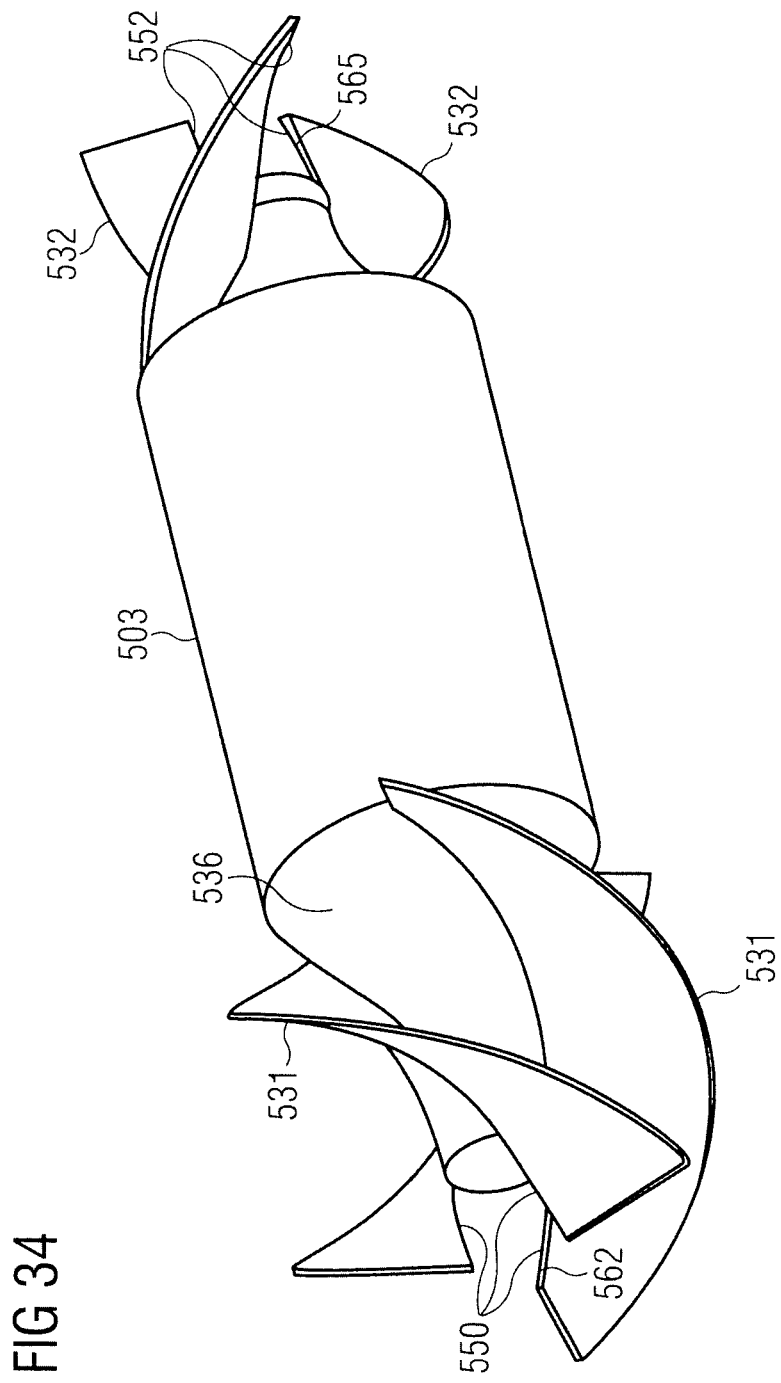
FIG. 34 shows the impeller of the blood pump of FIG. 33.
Figure 35:
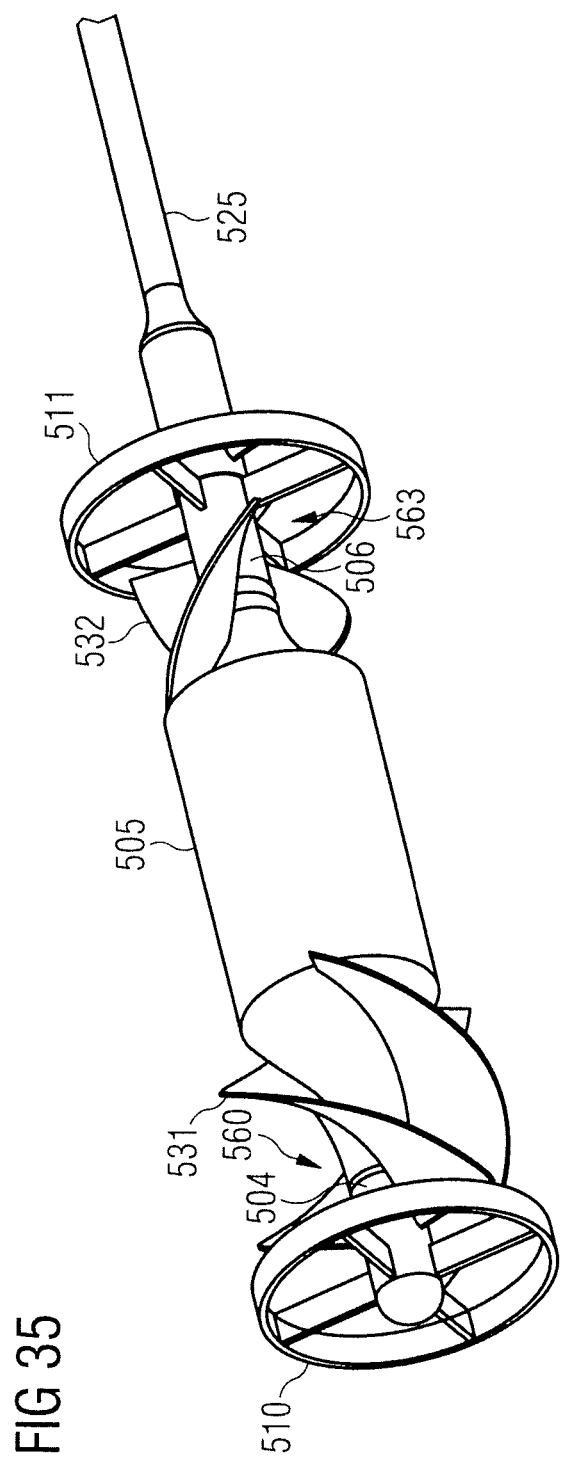
FIG. 35 shows the impeller along with the stationary bearing portions of the blood pump of FIG. 33.
Figure 36:
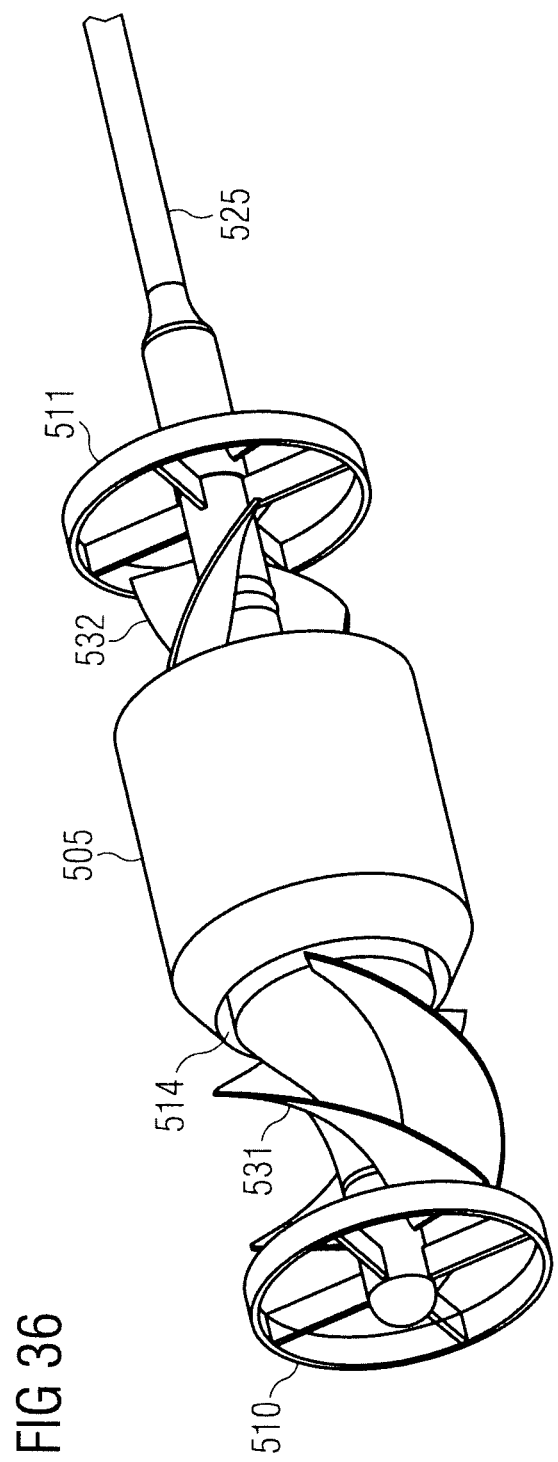
FIG. 36 shows the impeller along with the stationary bearing portions and the drive unit of the blood pump of FIG. 33.
Figure 37:
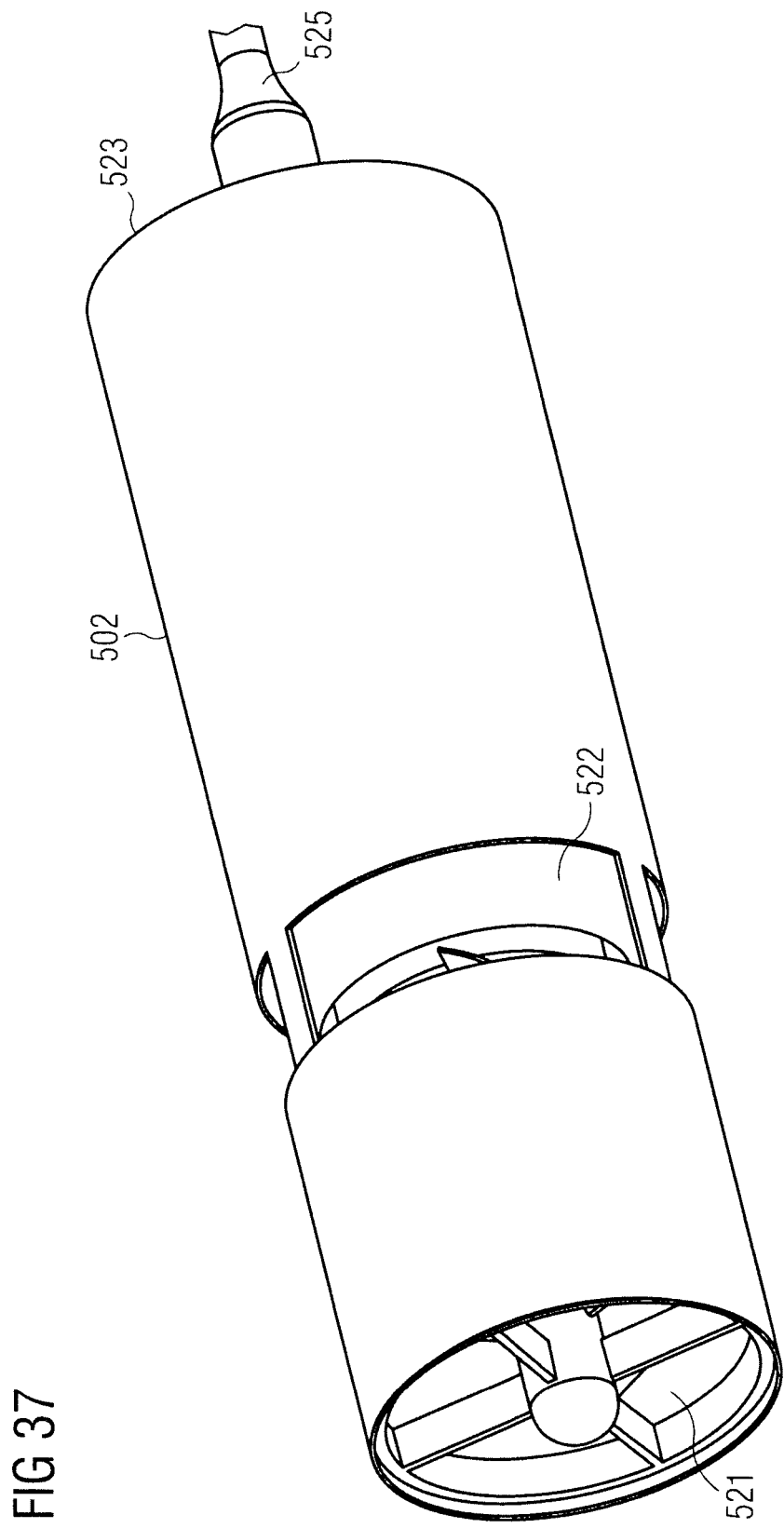
FIG. 37 shows a perspective view of the blood pump of FIG. 33.

The embodiment illustrated in FIG. 32 is substantially identical to that of FIG. 32 except that the shroud 740 is omitted. This provides a more open bearing design that may improve flushing of the bearing. The secondary blades 732 may be formed completely straight in an axial direction rather than helically as shown in FIGS. 31 and 32. This provides a secondary centrifugal pump to further improve flushing of the bearing. In particular, blood deposit is centrifuged radially outwards away from the inner edges 750 of the secondary blades 732. The impeller 703, in particular the secondary blades 732, can be easily manufactured. For instance, the tip 743 of the impeller 703 along with the secondary blades 732 can be manufactured as an injection molded ceramic element.

Referring to FIGS. 33 to 37, another embodiment of a blood pump is illustrated. It has an upstream portion that is substantially similar to the embodiment shown in FIGS. 28 to 30. The blood pump has a pump casing 502 with a blood flow inlet 521 and a blood flow outlet 522. The impeller 503 has outer blades 531 on an outer surface of the impeller hub 536 that form exposed radially inner edges 550 as described above. A bearing 560 is formed by bearing surfaces 562 on the exposed radially inner edges 550 and a stationary bearing surface 561 on a pin 504 of a stationary bearing portion 510. Due to the tapered shape of the impeller hub 536, a blood flow is directed radially outwards from the blood flow inlet 521 to the blood flow outlet 522. As explained above, magnets (not shown) that cause an axial repulsive force to adjust the axial position of the impeller 503 could be disposed in the impeller 503 and the pin 504, respectively.

In this embodiment, the impeller 503 has a second set of blades 532 in a downstream portion of the impeller 503 as well as a second bearing 563 that is substantially identical to the bearing 560. The blades 532 form exposed radially inner edges 552 that define rotating bearing surfaces 565 engaging a stationary bearing surface 564 on a pin 506. The pin 506 is included in another stationary bearing portion 511 that is substantially identical to the stationary bearing portion 510. It is connected to a catheter 525 that supplies e.g. electrical power to the blood pump. A secondary blood flow inlet 523 is formed in the downstream end portion of the pump casing 502. Apertures in the stationary bearing portion 511 allow blood to enter the impeller region from this side in a direction opposite the main direction of flow. The blades 532 are arranged to pump blood against the main direction of flow along an intermediate portion 530 of the impeller 503 through a gap 514 towards the blood flow outlet 522 as indicated by arrows. This allows flushing of the gap between the pump casing 502 and the intermediate portion 530 of the impeller 503 that includes a magnet 570 that is caused to rotate by an electric drive unit 505 circumferentially arranged about the impeller 503. The blades 532 are designed to cause enough backward flow to wash out the gap 514 but at the same time do not affect the main blood flow. In particular, the blades 532 may be smaller than the blades 531. In the other embodiments as well, any of the blades may have at their respective exposed radially inner edges a coating or insert comprising a material with improved heat-dissipating and wear-resisting properties, such as ceramics. The axial forces of the two axial impeller sections can be minimized due to the opposing pumping directions.

Figure 38:
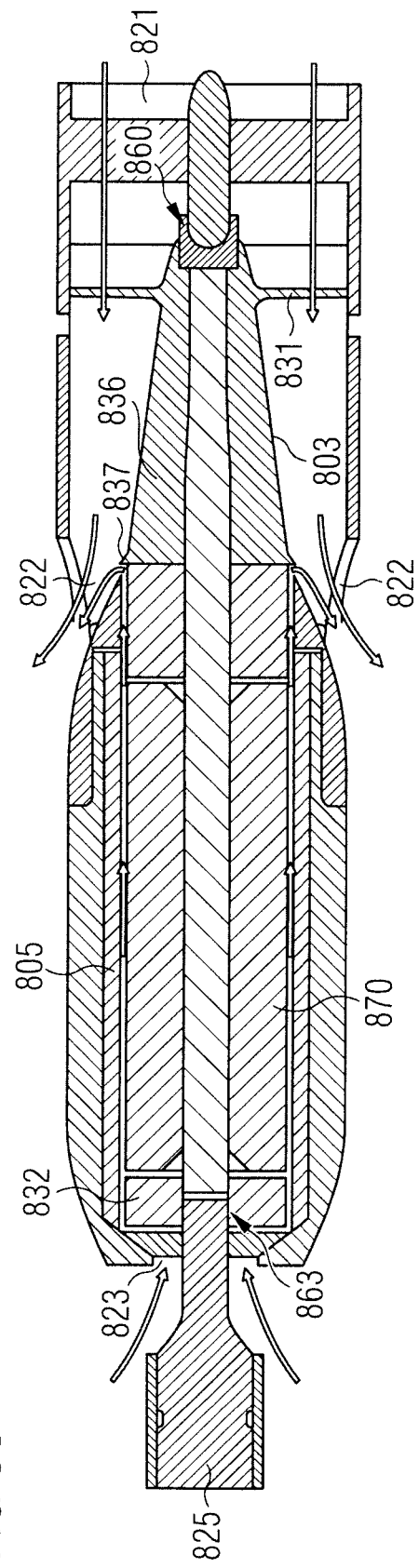
FIG. 38 shows a cross-sectional view of a blood pump according to another embodiment.

FIG. 38 shows another embodiment of a blood pump that is substantially similar to the embodiment shown in FIGS. 33 to 37. The impeller 803 has two sets of blades 831, 832 to form respective bearings 860, 863. The blades 831 cause a main blood flow from a blood flow inlet 821 to a blood flow outlet 822. As in the previous embodiment, secondary blades 832 cause a backward wash-out flow from a secondary blood flow inlet 823 through a gap between the stator coils 805 and the magnet 870 to the blood flow outlet. The secondary blood flow inlet 823 is directed towards the catheter 825. The impeller hub 836 has a shoulder 837 that circumferentially extends about the hub 836 in a region of the blood flow outlet 822 to direct the main blood flow and in particular the wash-out flow out of the blood flow outlet 822. That is to say, a local centrifugal and water jet pump is created due to the main flow passing across an almost perpendicular gap and the radial shoulder 837. It will be appreciated that the secondary blades 832 can be designed as a centrifugal pump with two or more blades, with the blades not being helically shaped but being straight to form a centrifugal pump.

Figure 39:
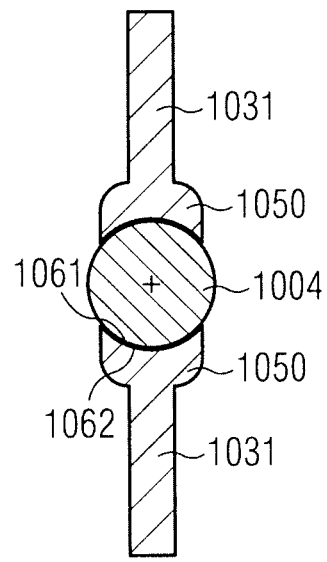
FIG. 39 shows a cross-sectional view of an embodiment of an impeller.
Figure 40:
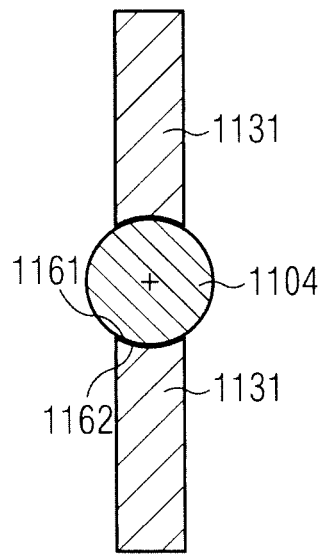
FIG. 40 shows a cross-sectional view of an embodiment of an impeller.

Any of the aforementioned blades can be designed in accordance with hydraulic requirements. In particular, the blades could be helical as shown in the embodiments. However, any of the aforementioned blades, in particular secondary blades as mentioned above, could be designed to form a centrifugal pump. In other words, the blades could be straight and could extend purely in an axial direction. FIG. 39 shows a cross-sectional view through straight blades 1031 engaging a pin 1004. The provision of a centrifugal pump having straight blades rather than helical blades may cause larger centrifugal forces, which facilitates removal of blood deposit from the bearing surfaces 1061, 1062 due to the higher density of blood deposit compared to blood. Deposit is conveyed radially outwards away from the bearing surfaces 1061, 1062, which helps to prevent blood clogging and clotting and therefore reduces the risk of thrombosis. The blades 1031 shown in FIG. 39 have an enlarged base 1050. FIG. 40 shows another embodiment wherein the blades 1131 engaging pin 1104 do not have an enlarged base. This may improve the centrifuging of blood deposit radially outwards away from the bearing surfaces 1161, 1162.

It will be appreciated that the described embodiments are only illustrative and not limiting. In particular, various aspects and features of the embodiments could be combined or independently employed in a different embodiment. For instance, the features and different designs described with respect to the outer blades, the inner blades, the pin, blood flow passages through the pin or the impeller, the drive unit, magnets for axial alignment, etc., could be variably combined without departing from the scope of the invention.

Preferred embodiments are described as the following items:

1. A blood pump comprises a pump casing having a blood flow inlet and a blood flow outlet, and an impeller arranged in said pump casing and rotatably supported in the pump casing by at least one bearing so as to be rotatable about an axis of rotation, the impeller having at least one blade for conveying blood from the blood flow inlet to the blood flow outlet, wherein the bearing comprises at least one stationary bearing portion coupled to the pump casing and having a stationary bearing surface that faces radially outwards, the bearing further comprising a rotating bearing surface interacting with the stationary bearing surface to form the bearing, wherein the rotating bearing surface faces radially inwards and is formed on an exposed radially inner edge of at least one of the at least one blade or on a bearing structure coupled to the exposed radially inner edge of the blade.

2. The blood pump of item 1, wherein the stationary bearing portion comprises at least one pin or cone extending along the axis of rotation.

3. The blood pump of item 1 or 2, wherein the stationary bearing portion is substantially cylindrical or tapered in shape.

4. The blood pump of any one of items 1 to 3, wherein the at least one stationary bearing portion extends axially along less than half of the length of the impeller or extends substantially along the entire length of the impeller.

5. The blood pump of any one of items 1 to 4, comprising two bearings, each having a stationary bearing portion, the stationary bearing portions axially extending into the impeller at opposing axial ends of the impeller.

6. The blood pump of any one of items 1 to 5, wherein the rotating bearing surface extends along substantially the entire length of the exposed radially inner edge of the at least one blade or only extends along a portion of the length of the exposed radially inner edge of the at least one blade.

7. The blood pump of any one of items 1 to 6, wherein the stationary bearing portion has a central axial passage extending therethrough.

8. The blood pump of any one of items 1 to 7, wherein the stationary bearing portion is coupled to the pump casing by means of a supporting structure that comprises at least one aperture to allow blood to pass therethrough in an axial direction.

9. The blood pump of any one of items 1 to 8, wherein the stationary bearing portion is coupled to the pump casing by means of a supporting structure that is sized and shaped to direct a blood flow in a radial direction.

10. The blood pump of any one of items 1 to 9, wherein the at least one blade is arranged on at least one of an outer surface of a hub of the impeller and an inner surface of the hub of the impeller.

11. The blood pump of any one of items 1 to 10, wherein the at least one blade is arranged on an outer surface of the impeller hub and axially extends beyond the hub.

12. The blood pump of any one of items 1 to 11, wherein the impeller has a blood flow passage extending through a hub of the impeller, wherein the impeller comprises at least one outer blade disposed on an outer surface of the impeller hub and sized and shaped for conveying blood from the blood flow inlet to the blood flow outlet, and at least one inner blade disposed in the passage and sized and shaped for conveying blood through the passage.

13. The blood pump of item 12, wherein the rotating bearing surface is formed on an exposed radially inner edge of at least one of the inner blade and the outer blade.

14. The blood pump of item 12 or 13, comprising two bearings, each having a stationary bearing portion, the stationary bearing portions axially extending into the impeller at opposing axial ends of the impeller, wherein the rotating bearing surface of one of the bearings is formed on an exposed radially inner edge of the at least one inner blade and the rotating bearing surface of the other one of the bearings is formed on an exposed radially inner edge of the at least one outer blade.

15. The blood pump of any one of items 12 to 14, wherein the passage of the impeller extends at least partially or completely along the axis of rotation.

16. The blood pump of item 15, wherein the at least one stationary bearing portion extends along at least half or at least three quarters of the length of the passage of the impeller, or extends completely through the passage of the impeller.

17. The blood pump of any one of items 12 to 16, wherein the at least one blade is arranged on the impeller such that the blade is divided by the hub of the impeller into an inner portion forming the inner blade and an outer portion forming the outer blade.

18. The blood pump of any one of items 12 to 17, wherein a maximum diameter of the stationary bearing portion is smaller than a minimum diameter of the passage of the impeller.

19. The blood pump of any one of items 1 to 18, wherein the pump casing has a secondary blood flow inlet axially spaced from the blood flow inlet and the blood flow outlet in a main direction of flow.

20. The blood pump of item 19, wherein the impeller comprises at least two blades, at least one of which is associated with the blood flow inlet in order to convey blood from the blood flow inlet to the blood flow outlet in a main direction of flow, and at least another one of which is associated with the secondary blood flow inlet to convey blood from the secondary blood flow inlet to the blood flow outlet in a direction opposite the main direction of flow.

21. The blood pump of item 20, wherein the at least two blades are arranged at axially opposing portions of the impeller adjacent an intermediate portion, and the at least one blade associated with the secondary blood flow inlet is sized and shaped to convey blood along the intermediate portion of the impeller.

22. The blood pump of any one of items 1 to 21, wherein the bearing structure comprises at least one of at least one ring surrounding at least a portion of the stationary bearing portion and at least one wing engaging at least a portion of the stationary bearing portion.

23. The blood pump of any one of items 1 to 22, wherein the rotating bearing surface is sized and shaped to engage an axial end of the stationary bearing portion.

24. The blood pump of any one of items 1 to 23, comprising an electric motor for driving the impeller, wherein a stator of the electric motor is coupled to the pump casing and circumferentially arranged about the impeller.

25. The blood pump of item 24, wherein the stator of the electric motor comprises at least one electrical arrangement for creating a rotating magnetic field and the impeller comprises at least one permanent magnet.

26. The blood pump of any one of items 1 to 25, wherein the stationary bearing portion and the impeller each comprise at least one magnet, the magnet in the stationary bearing portion and the magnet in the impeller being radially aligned and arranged in the stationary bearing portion and the impeller, respectively, such that an axial repulsive magnetic force is caused between the stationary bearing portion and the impeller.

27. The blood pump of any one of items 1 to 26, wherein at least one of the stationary bearing surface and the rotating bearing surface comprises a material having a greater hardness than a material of the rest of the stationary bearing portion and the impeller, respectively.

28. The blood pump of any one of items 1 to 27, wherein the impeller includes at least one secondary blade disposed at an axial end surface of the impeller.

29. The blood pump of item 28, wherein the secondary blades form part of a hydrodynamic bearing.

30. A blood pump comprises a pump casing having a blood flow inlet and a blood flow outlet, and an impeller arranged in said pump casing so as to be rotatable about an axis of rotation, the impeller having a blood flow passage extending through a hub of the impeller, wherein the impeller comprises outer blades disposed on an outer surface of the hub of the impeller and sized and shaped for conveying blood from the blood flow inlet to the blood flow outlet, and inner blades disposed in the passage and sized and shaped for conveying blood through the passage.

31. The blood pump of item 30, wherein the impeller is rotatably supported in the pump casing by at least one bearing, wherein the inner blades disposed in the passage are sized and shaped for conveying blood through the passage to the bearing.

32. The blood pump of item 30 or 31, wherein the passage of the impeller extends at least partially or completely along the axis of rotation.

33. The blood pump of any one of items 30 to 32, wherein the impeller comprises a bearing structure that is disposed in the passage.

34. The blood pump of item 33, further comprising at least one pin extending along the axis of rotation, wherein at least a portion of the pin engages the bearing structure of the impeller to form the at least one bearing.

35. The blood pump of item 34, wherein the pin extends at least half or at least three quarters along the length of the passage of the impeller, or extends completely through the passage of the impeller.

36. The blood pump of item 34 or 35, wherein a maximum diameter of the pin is smaller than a minimum diameter of the passage of the impeller.

37. The blood pump of any one of items 33 to 36, wherein the inner blades of the impeller form part of the bearing structure of the impeller and have at least one radially inner edge that defines a bearing surface.

38. The blood pump of item 37 and item 34, wherein at least a portion of the at least one radially inner edge of the inner blades engages at least a portion of a circumferential surface of the pin to form the at least one bearing.

39. The blood pump of any one of items 34 to 36, wherein the bearing structure of the impeller comprises at least one ring engaging at least a portion of the pin.

40. The blood pump of any one of items 34 to 36, wherein the bearing structure of the impeller comprises at least one wing engaging at least a portion of the pin.

41. The blood pump of any one of items 34 to 36, wherein the bearing structure of the impeller comprises at least one bearing surface that is sized and shaped to engage an axial end of the pin to form the at least one bearing.

42. The blood pump of any one of items 30 to 41, wherein the inner blades are aligned with the outer blades.

43. The blood pump of any one of items 1 to 42, wherein the blood pump is an intravascular blood pump.

44. The blood pump of any one of items 1 to 43, wherein the blood pump is an axial blood pump, a centrifugal blood pump or a mixed-type blood pump.

The invention claimed is:

1. A blood pump, comprising:
a pump casing having a blood flow inlet and a blood flow outlet,
an impeller arranged in said pump casing and rotatably supported in the pump casing by at least one bearing so as to be rotatable about an axis of rotation, the impeller having at least one blade for conveying blood from the blood flow inlet to the blood flow outlet,
wherein the at least one bearing comprises at least one stationary bearing portion coupled to the pump casing by means of a supporting structure that comprises at least one aperture to allow blood to pass therethrough in an axial direction and having a stationary bearing surface that faces radially outwards, the at least one bearing further comprising a rotating bearing surface interacting with the stationary bearing surface to form the at least one bearing, and
wherein the rotating bearing surface faces radially inwards and is formed on an exposed radially inner edge of at least one of the at least one blade thereby, in operation, drawing a blood deposit from the stationary bearing surface in a radially outward direction.

2. The blood pump of claim 1,
wherein the at least one stationary bearing portion comprises at least one pin or cone extending along the axis of rotation, the at least one stationary bearing portion being substantially cylindrical or tapered in shape.

3. The blood pump of claim 2, wherein the at least one stationary bearing portion has a central axial passage extending therethrough.

4. The blood pump of claim 1, comprising two bearings, each having a stationary bearing portion, the stationary bearing portions axially extending into the impeller at opposing axial ends of the impeller.

5. The blood pump of claim 1,
wherein the at least one blade is arranged on at least one of an outer surface of a hub of the impeller and an inner surface of the hub of the impeller, and wherein, when the at least one blade is arranged on the outer surface of the hub of the impeller, the at least one blade axially extends beyond the hub of the impeller.

6. The blood pump of claim 1,
wherein the impeller has a blood flow passage extending through a hub of the impeller, wherein the impeller comprises at least one outer blade disposed on an outer surface of the hub and sized and shaped for conveying blood from the blood flow inlet to the blood flow outlet, and at least one inner blade disposed in the blood flow passage and sized and shaped for conveying blood through the blood flow passage, and
wherein the rotating bearing surface is formed on an exposed radially inner edge of at least one of the at least one inner blade and the at least one outer blade.

7. The blood pump claim 6, wherein the at least one blade is arranged on the impeller such that the blade is divided by the hub of the impeller into an inner portion forming the at least one inner blade and an outer portion forming the at least one outer blade.

8. The blood pump of claim 6, wherein the at least one stationary bearing portion extends completely through the blood flow passage.

9. The blood pump of claim 6,
wherein the blood flow passage of the impeller extends at least partially along the axis of rotation, and
wherein the at least one stationary bearing portion extends along at least half of a length of the blood flow passage of the impeller.

10. The blood pump of claim 9, wherein the impeller has at least one radial opening to connect the blood flow passage with an environment of the impeller.

11. The blood pump of claim 1, wherein the pump casing has a secondary blood flow inlet axially spaced from the blood flow inlet and the blood flow outlet in a main direction of flow,
wherein the impeller comprises at least two blades, at least one of which is associated with the blood flow inlet in order to convey blood from the blood flow inlet to the blood flow outlet in a main direction of flow, and at least another one of which is associated with the secondary blood flow inlet to convey blood from the secondary blood flow inlet to the blood flow outlet in a direction opposite the main direction of flow, and
wherein the at least two blades are arranged at axially opposing portions of the impeller adjacent an intermediate portion.

12. The blood pump of claim 11, wherein the at least one blade associated with the secondary blood flow inlet is sized and shaped to convey blood along the intermediate portion of the impeller.

13. The blood pump of claim 1,
wherein a bearing structure of the at least one bearing comprises at least one of at least one ring surrounding at least a portion of the at least one stationary bearing portion and at least one wing engaging at least a portion of the at least one stationary bearing portion.

14. The blood pump of claim 1, comprising an electric motor for driving the impeller,
wherein a stator of the electric motor is coupled to the pump casing and circumferentially arranged about the impeller, and
wherein the stator of the electric motor comprises at least one electrical arrangement for creating a rotating magnetic field and the impeller comprises at least one permanent magnet.

15. The blood pump of claim 1,
wherein the at least one stationary bearing portion and the impeller each comprise at least one magnet, the magnet in the stationary bearing portion and the magnet in the impeller being radially aligned and arranged in the stationary bearing portion and the impeller, respectively, such that an axial repulsive magnetic force is caused between the stationary bearing portion and the impeller.

16. The blood pump of claim 1, wherein at least one of the stationary bearing surface and the rotating bearing surface comprises a material having a greater hardness than a material of the rest of the at least one stationary bearing portion and the impeller, respectively.

17. The blood pump of claim 1, wherein at least one of the at least one ring and the at least one wing defines an additional bearing surface, the additional bearing surface sized and shaped to engage an axial end of the at least one stationary bearing portion.

18. The blood pump of claim 1, wherein the supporting structure is sized and shaped to direct a blood flow in a radial direction.

19. The blood pump of claim 1, wherein the impeller comprises at least one secondary blade disposed on an axial end surface of the impeller.

20. The blood pump of claim 19, wherein the at least one secondary blade is provided on a downstream end surface of the impeller in a gap.

21. The blood pump of claim 19, wherein the at least one secondary blade forms part of a hydrodynamic bearing.

22. A blood pump, comprising:
a pump casing having a blood flow inlet and a blood flow outlet,
an impeller arranged in said pump casing and rotatably supported in the pump casing by at least one bearing so as to be rotatable about an axis of rotation, the impeller having at least one blade for conveying blood from the blood flow inlet to the blood flow outlet,
wherein the at least one bearing comprises at least one stationary bearing portion coupled to the pump casing and having a stationary bearing surface that faces radially outwards, the at least one bearing further comprising a rotating bearing surface interacting with the stationary bearing surface to form the at least one bearing, and
wherein the rotating bearing surface faces radially inwards and is formed on a bearing structure coupled to an exposed radially inner edge of the blade.

23. A blood pump, comprising:
a pump casing having a blood flow inlet and a blood flow outlet,
an impeller arranged in said pump casing and rotatably supported in the pump casing by at least one bearing so as to be rotatable about an axis of rotation, the impeller having at least one blade for conveying blood from the blood flow inlet to the blood flow outlet, wherein the at least one blade is arranged on at least one of an outer surface of a hub of the impeller and an inner surface of the hub of the impeller, and wherein, when the at least one blade is arranged on the outer surface of the hub of the impeller, the at least one blade axially extends beyond the hub of the impeller;
wherein the at least one bearing comprises at least one stationary bearing portion coupled to the pump casing and having a stationary bearing surface that faces radially outwards, the at least one bearing further comprising a rotating bearing surface interacting with the stationary bearing surface to form the at least one bearing; and wherein the rotating bearing surface faces radially inwards and is formed on an exposed radially inner edge of at least one of the at least one blade thereby, in operation, drawing a blood deposit from the stationary bearing surface in a radially outward direction.

24. A blood pump, comprising:

a pump casing having a blood flow inlet and a blood flow outlet, an impeller arranged in said pump casing and rotatably supported in the pump casing by at least one bearing so as to be rotatable about an axis of rotation, the impeller has a blood flow passage extending through a hub of the impeller, wherein the impeller comprises at least one outer blade disposed on an outer surface of the hub and sized and shaped for conveying blood from the blood flow inlet to the blood flow outlet, and at least one inner blade disposed in the blood flow passage and sized and shaped for conveying blood through the blood flow passage, wherein the at least one bearing comprises at least one stationary bearing portion coupled to the pump casing and having a stationary bearing surface that faces radially outwards, the at least one bearing further comprising a rotating bearing surface interacting with the stationary bearing surface to form the at least one bearing, and wherein the rotating bearing surface faces radially inwards and is formed on an exposed radially inner edge of at least one of the at least one inner blade and the at least one outer blade.

25. The blood pump of claim 24, comprising two bearings, each having a stationary bearing portion, the stationary bearing portions axially extending into the impeller at opposing axial ends of the impeller, wherein a-rotating bearing surface of one of the two bearings is formed on an exposed radially inner edge of the at least one inner blade and a rotating bearing surface of the other one of the two bearings is formed on an exposed radially inner edge of the at least one outer blade.

26. A blood pump, comprising:

a pump casing having a blood flow inlet and a blood flow outlet, an impeller arranged in said pump casing and rotatably supported in the pump casing by at least one bearing so as to be rotatable about an axis of rotation, the impeller having at least one blade for conveying blood from the blood flow inlet to the blood flow outlet, wherein the at least one bearing comprises at least one stationary bearing portion coupled to the pump casing and having a stationary bearing surface that faces radially outwards, the at least one bearing further comprising a rotating bearing surface interacting with the stationary bearing surface to form the at least one bearing, wherein at least one of the stationary bearing surface and the rotating bearing surface comprises a material having a greater hardness than a material of the rest of the at least one stationary bearing portion and the impeller, respectively; and wherein the rotating bearing surface faces radially inwards and is formed on an exposed radially inner edge of at least one of the at least one blade.

27. A blood pump, comprising:

a pump casing having a blood flow inlet and a blood flow outlet, an impeller arranged in said pump casing and rotatably supported in the pump casing by at least one bearing so as to be rotatable about an axis of rotation, the impeller having at least one blade for conveying blood from the blood flow inlet to the blood flow outlet, two bearings, each having a stationary bearing portion coupled to the pump casing, the stationary bearing portions axially extending into the impeller at opposing axial ends of the impeller and at least one bearing having a stationary bearing surface that faces radially outwards, the at least one bearing further comprising a rotating bearing surface interacting with the stationary bearing surface to form the at least one bearing, and wherein the rotating bearing surface faces radially inwards and is formed on an exposed radially inner edge of at least one of the at least one blade thereby, in operation, drawing a blood deposit from the stationary bearing surface in a radially outward direction.

* * * * *

UNITED STATES PATENT AND TRADEMARK OFFICE
CERTIFICATE OF CORRECTION

PATENT NO. : 10,780,208 B2
APPLICATION NO. : 15/750001
DATED : September 22, 2020
INVENTOR(S) : Siess et al.

Page 1 of 1

It is certified that error appears in the above-identified patent and that said Letters Patent is hereby corrected as shown below:

In the Specification

Column 13, Line 52:
Now reads: "261, 261"; should read -- 261, 262 --

In the Claims

Column 21, Claim 7, Line 17:
Now reads: "blood pump"; should read -- blood pump of --

Signed and Sealed this
Eighth Day of February, 2022

Drew Hirshfeld
*Performing the Functions and Duties of the*
*Under Secretary of Commerce for Intellectual Property and*
*Director of the United States Patent and Trademark Office*